(12) United States Patent
Green et al.

(10) Patent No.: US 8,658,693 B2
(45) Date of Patent: Feb. 25, 2014

(54) 4-AMINOBENZONITRILE SELECTIVE ANDROGEN RECEPTOR MODULATORS

(71) Applicant: Eli Lilly and Company, Indianapolis, IN (US)

(72) Inventors: Jonathan Edward Green, Avon, IN (US); Prabhakar Kondaji Jadhav, Zionsville, IN (US); Venkatesh Krishnan, Fishers, IN (US); Donald Paul Matthews, Indianapolis, IN (US); Ashraf Saeed, Carmel, IN (US); Gregory Alan Stephenson, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 13/645,535

(22) Filed: Oct. 5, 2012

(65) Prior Publication Data

US 2013/0217762 A1 Aug. 22, 2013

Related U.S. Application Data

(60) Provisional application No. 61/546,711, filed on Oct. 13, 2011.

(51) Int. Cl.
*C07D 309/14* (2006.01)
*C07D 307/22* (2006.01)
*C07C 255/58* (2006.01)
*A61K 31/341* (2006.01)
*A61K 31/351* (2006.01)
*A61K 31/277* (2006.01)
*A61P 5/26* (2006.01)

(52) U.S. Cl.
USPC ........... 514/472; 514/549; 514/646; 549/419; 549/475; 558/418

(58) Field of Classification Search
CPC ... C07D 309/14; C07D 307/24; C07C 255/58
USPC .................. 549/419, 475; 558/418
See application file for complete search history.

(56) References Cited

U.S. PATENT DOCUMENTS 3,594,405 A * 7/1971 Loux .............................. 549/424
8,519,158 B2 * 8/2013 Zhi et al. ........................ 548/577
2008/0269193 A1 * 10/2008 Huang et al. ............. 514/212.03

FOREIGN PATENT DOCUMENTS

WO 2006124447 11/2006
WO 2008130879 10/2008
WO 2009105214 8/2009

OTHER PUBLICATIONS

Burks et al. "Losartan Restores Skeletal Muscle Remodeling and Protects Against Disuse Atrophy in Sarcopenia." Sci. Transl. Med. 2011, 3(82), 82ra37 (published online May 31, 2011).*

* cited by examiner

*Primary Examiner* — Alicia L Otton
*Assistant Examiner* — Amanda L Aguirre
(74) *Attorney, Agent, or Firm* — Elizabeth A. Dingess-Hammond

(57) ABSTRACT

The present invention provides novel selective androgen receptor modulators and their salts and pharmaceutical compositions thereof.

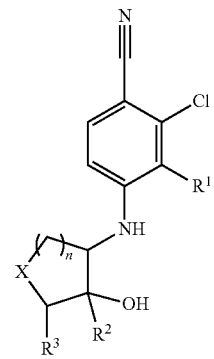

23 Claims, 4 Drawing Sheets

X-ray powder diffraction pattern of Example 1C, 2-chloro-4-[[(1R,2R)-2-hydroxy-2-methyl-cyclopentyl]amino]-3-methyl-benzonitrile crystalline Form 1.

2-Theta

X-ray powder diffraction pattern of Example 1D, 2-chloro-4-[[(1R,2R)-2-hydroxy-2-methyl-cyclopentyl]amino]-3-methyl-benzonitrile crystalline Form 2.

2-Theta

X-ray powder diffraction pattern of Example 1E, 2-chloro-4-[[(1R,2R)-2-hydroxy-2-methyl-cyclopentyl]amino]-3-methyl-benzonitrile crystalline ethanol solvate.

2-Theta

X-ray powder diffraction pattern of Example 1F, 2-chloro-4-[[(1R,2R)-2-hydroxy-2-methyl-cyclopentyl]amino]-3-methyl-benzonitrile crystalline isopropanol solvate.

4-AMINOBENZONITRILE SELECTIVE ANDROGEN RECEPTOR MODULATORS

The androgen receptor (AR) is part of the steroid nuclear hormone receptor subfamily that also includes the mineralocortocoid receptor (MR), the progesterone receptor (PR), the estrogen receptor (ER), and the glucocorticoid receptor (GR). Endogenous steroidal androgens (e.g. testosterone and 5α-dihydrotestosterone (DHT)) are the major circulating sex hormones and play a role in the regulation of various physiological processes. Anabolic (e.g. tissue building) effects of androgens include increasing muscle mass and strength and increasing bone mass and density, whereas androgenic (e.g. masculinizing) effects include development of the internal reproductive tissues (e.g. prostate and seminal vesicles), the external genitalia, male hair growth patterns, and libido. Clinically, androgen replacement therapy has been used in the treatment of various conditions and disorders including male hypogonadism, muscle wasting diseases, and cachexia.

However, steroidal androgen therapy is limited. For example, preparations of steroidal androgens have been found to suffer from rapid degradation in the liver leading to poor oral bioavailability and short duration of activity following parenteral administration, variations in plasma levels, hepatotoxicity, or cross reactivity with other steroid hormone receptors, such as GR, MR, and PR. Further, it has been observed that oral anabolic non-steroidal and steroidal androgens produce greater lowering of high-density lipoprotein (HDL) in eugonadal men and women relative to parenteral androgens. Lowering of HDL has been suggested to result in poor cardiovascular health outcomes.

Therefore, there remains a need for alternatives to steroidal androgen therapy. More particularly, there remains a need for nonsteroidal AR agonists which bind to AR with greater affinity relative to the other steroid hormone receptors. Even more particularly, there remains a need for tissue-selective androgen receptor modulators (SARMs) which display androgen agonist activity in anabolic tissues such as muscle or bone, but only partial agonist, partial antagonist or antagonist activity in androgenic tissues such as the prostate or seminal vesicle. SARMs may provide the benefits of traditional anabolic steroids, such as muscle or bone growth, while minimizing the proliferative or hypertrophic effects on sex tissues.

Published international patent applications, WO09/105,214 and WO06/124447, disclose small molecule, non-steroidal SARMs. Still, there exists a need for new non-steroidal SARM compounds with improved potency and/or pharmacokinetic characteristics, such as exposure bioavialability. There also exists a need for efficacious SARM compounds. Additionally, there exists a need for SARM compounds that build muscle mass without the side effect of prostate gland enlargement. Androgens and SARM compounds are known to decrease HDL at efficacious exposures when delivered via oral route. Thus, there exists a need for SARM compounds that do not significantly decrease HDL levels. The present invention provides preferred androgen receptor modulating compounds which have a minimum risk of HDL lowering at efficacious doses when delivered via a transdermal route.

Therefore, the present invention provides novel compounds which are AR agonists. More preferably, the compounds are SARMs. Such new compounds could address the need for potent, effective treatment of muscle atrophy, hypogonadism, or cachexia with minimum risk of prostate enlargement or HDL lowering.

The present invention provides a compound of formula:

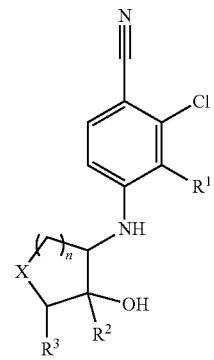

wherein
n is 1 or 2;
X is —CH$_2$— or —O—;
R$^1$ is —CH$_3$ or —CH$_2$CH$_3$;
R$^2$ is —H or —CH$_3$;
R$^3$ is —H or —OH;
wherein R$^3$ is —H when X is —O—;
or a pharmaceutically acceptable salt thereof.

The present invention further provides a method for the treatment or prevention of muscle atrophy in a patient comprising administering to a patient in need of such treatment or prevention an effective amount of a compound of the present invention, or a pharmaceutically acceptable salt thereof. In a particular aspect, the present invention provides a method of treating or preventing muscle atrophy associated with disuse, trauma, immobilization, spinal cord injury, or stroke comprising administering to a patient in need thereof an effective amount of a compound of the present invention. Even more particularly, the present invention provides a method of treating or preventing muscle atrophy associated with hip or knee replacement, hip fracture, spinal cord injury, or stroke comprising administering to a patient in need thereof an effective amount of a compound of the present invention.

Additionally, the present invention provides a pharmaceutical formulation comprising a compound of the invention, or a pharmaceutically acceptable salt thereof, and a pharmaceutically acceptable carrier, diluent, or excipient. The present invention provides a pharmaceutical composition comprising a compound of the invention, or a pharmaceutically acceptable salt thereof, and one or more pharmaceutically acceptable carriers, diluents, or excipients. In a further embodiment, the present invention provides a pharmaceutical composition comprising a solvate, wherein the solvate molecules include ethanol and isopropanol. In a further embodiment, the present invention provides a pharmaceutical composition for the treatment or prevention of muscle atrophy associated with hip or knee replacement, hip fracture, spinal cord injury, or stroke comprising a compound of the invention in combination with one or more pharmaceutically acceptable carriers, diluents or excipients. In yet a further embodiment, the pharmaceutical composition further comprises one or more other therapeutic agents. In another embodiment, the pharmaceutical composition has minimal risk of lowering HDL.

Further, the present invention provides a compound of the invention, or a pharmaceutically acceptable salt thereof, for use in therapy, in particular for treating or preventing muscle atrophy. Even further, the present invention provides a compound of the invention, or a pharmaceutically acceptable salt thereof, for use in treating muscle atrophy. In a further embodiment, the present invention provides a compound of the invention, or a pharmaceutically acceptable salt thereof, for use in therapy, in particular for treating or preventing muscle atrophy associated with hip or knee replacement, hip fracture, spinal cord injury, or stroke. Even further, the present invention provides a compound of the invention, or a pharmaceutically acceptable salt thereof, for use in treating or preventing muscle atrophy associated with hip or knee replacement, hip fracture, spinal cord injury, or stroke. Furthermore, the present invention provides the use of a compound of the invention, or a pharmaceutically acceptable salt thereof, for the manufacture of a medicament for treating or preventing muscle atrophy. In a further embodiment, the present invention provides the use of a compound of the invention, or a pharmaceutically acceptable salt thereof, for the manufacture of a medicament for treating or preventing muscle atrophy associated with hip or knee replacement, hip fracture, spinal cord injury, or stroke.

The present invention also provides a method of treating or preventing hypogonadism or cachexia by administering an effective amount of a compound of the present invention, or a pharmaceutically acceptable salt thereof. The present invention further provides a method for the treatment or prevention of hypogonadism or cachexia in a patient comprising administering to a patient in need of such treatment or prevention an effective amount of a compound of the present invention, or a pharmaceutically acceptable salt thereof. Further, the present invention provides a compound of the invention or a pharmaceutically acceptable salt thereof for use in therapy, in particular for treating or preventing hypogonadism. Even further, the present invention provides a compound of the invention, or a pharmaceutically acceptable salt thereof, for use in treating or preventing hypogonadism. Also, the present invention provides a compound of the invention, or a pharmaceutically acceptable salt thereof, for use in therapy, in particular for treating or preventing cachexia. Even further, the present invention provides a compound of the invention, or a pharmaceutically acceptable salt thereof, for use in treating or preventing cachexia. Furthermore, the present invention provides the use of a compound of the invention, or a pharmaceutically acceptable salt thereof, for the manufacture of a medicament for treating or preventing hypogonadism or cachexia. The present invention provides the use of a compound of the invention, or a pharmaceutically acceptable salt thereof, for the manufacture of a medicament for the treatment or prevention of hypogonadism or cachexia.

The present invention also provides a method of preventing fall-related injuries in elderly fallers with muscle weakness by administering an effective amount of a compound of the present invention, or a pharmaceutically acceptable salt thereof. The present invention further provides a method for the prevention of fall-related injuries in elderly fallers with muscle weakness by administering an effective amount of a compound of the present invention, or a pharmaceutically acceptable salt thereof. Further, the present invention provides a compound of the invention or a pharmaceutically acceptable salt thereof for use in therapy, in particular for preventing fall-related injuries in elderly fallers with muscle weakness. Even further, the present invention provides a compound of the invention, or a pharmaceutically acceptable salt thereof, for use in preventing fall-related injuries in elderly fallers with muscle weakness. Furthermore, the present invention provides the use of a compound of the invention, or a pharmaceutically acceptable salt thereof, for the manufacture of a medicament for preventing fall-related injuries in elderly fallers with muscle weakness.

The present invention also provides a method of reversing, treating, or preventing the adverse effects of androgen deprivation therapy (ADT) by administering an effective amount of a compound of the present invention, or a pharmaceutically acceptable salt thereof. The present invention further provides a method for the reversal, treatment, or prevention of the adverse effects of ADT in a patient comprising administering to a patient in need of such treatment or prevention an effective amount of a compound of the present invention, or a pharmaceutically acceptable salt thereof. Further, the present invention provides a compound of the invention or a pharmaceutically acceptable salt thereof for use in therapy, in particular for reversing, treating, or preventing the adverse effects of ADT. Even further, the present invention provides a compound of the invention, or a pharmaceutically acceptable salt thereof, for use in reversing, treating, or preventing the adverse effects of ADT. Furthermore, the present invention provides the use of a compound of the invention, or a pharmaceutically acceptable salt thereof, for the manufacture of a medicament for reversing, treating, or preventing the adverse effects of ADT.

The present invention also encompasses intermediates and processes useful for the synthesis of a compound of the present invention.

A particular method in which a compound of the present invention is believed useful is in the treatment or prevention of muscle wasting conditions or muscle atrophy. Muscle wasting may occur as a natural result of aging (e.g. sarcopenia). Alternatively, muscle atrophy may result as a secondary consequence of disuse or inactivity (e.g. following hip or knee replacement or hip fracture), trauma, immobilization (e.g. casting or splinting of limbs), as well as spinal cord injury or stroke. (See, Hafer-Macko et al., *J. Rehab. Res. Develop.*; 45(2): 261-272 (2008)) Thus, the term "muscle atrophy," as used herein, is synonymous with muscle wasting and refers to a condition wherein a patient has lost muscle mass due to a health condition such as cancer, HIV, or as a result of extended period(s) of inactivity or as an adjunct treatment following surgery where significant periods of inactivity have or may have resulted in loss of muscle mass. Further as used herein, the term "muscle atrophy associated with disuse, trauma, immobilization, spinal cord injury or stroke" refers to muscle atrophy that occurs as a secondary consequence to the incidence of disuse or inactivity (e.g. following hip or knee replacement or hip fracture), trauma, immobilization (e.g. casting or splinting of limbs), spinal cord injury or stroke. Furthermore, in the context of spinal cord injury or stroke, a compound of the present invention may be used as an adjunct to standard rehabilitation therapy (e.g. physical or occupational therapy, exercise, assisted walking, and/or strength training). Even further, a compound of the present invention may be used for treating or preventing co-morbidities as a result of falls due to lower limb muscle atrophy as evidenced by changes in objective measurements that assess risk of falls in the elderly (See Close and Lord, *BMJ* 2011; 343:d5153).

Another particular method in which a compound of the present invention is believed useful is in the reversal, treatment, or prevention of the adverse effects of hormone therapy for prostate cancer, also called androgen deprivation therapy (ADT) or androgen suppression therapy.

Figure 1:
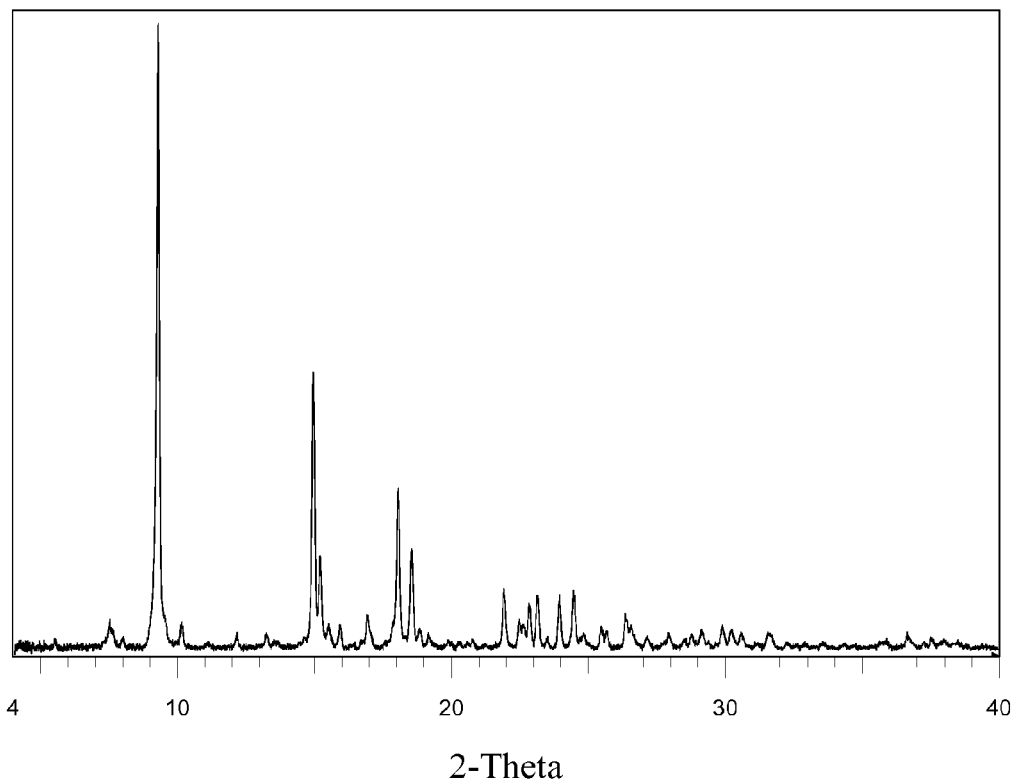
FIG. 1 is a spectrogram of a representative X-ray powder diffraction (XRD) pattern for 2-chloro-4-[[(1R,2R)-2-hydroxy-2-methyl-cyclopentyl]amino]-3-methyl-benzonitrile crystalline Form 1. The XRD spectrogram was obtained as described in the Example 1C below.
Figure 2:
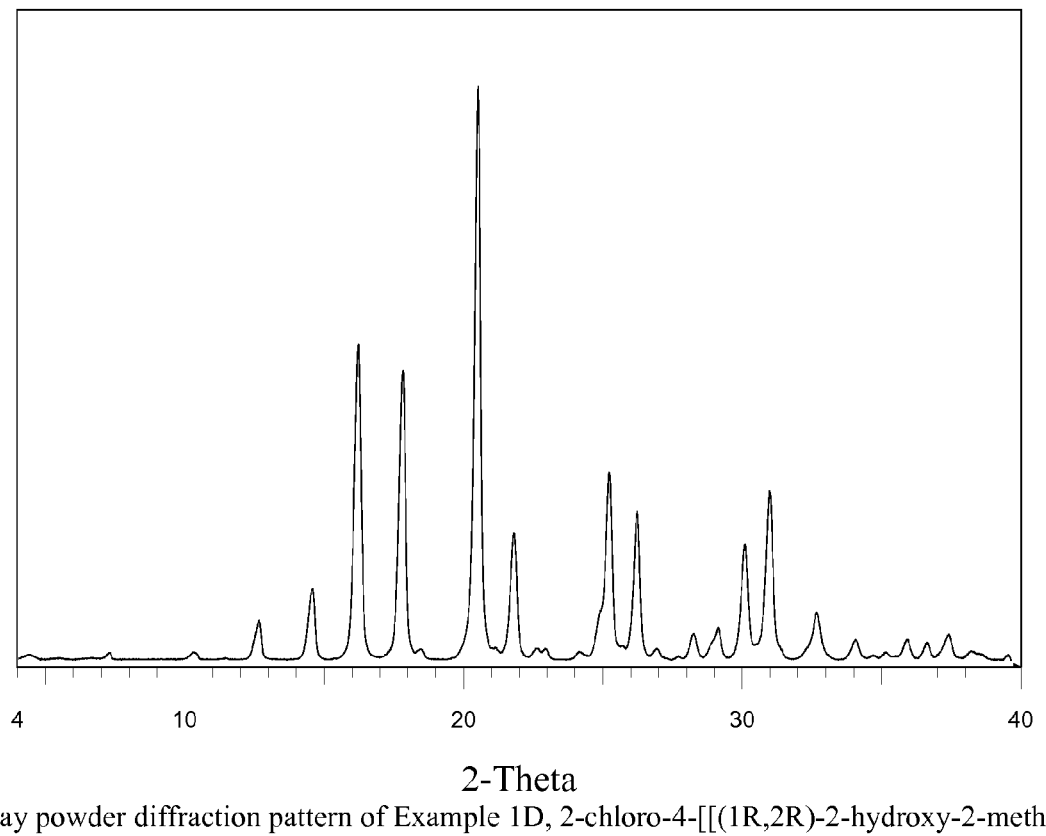
FIG. 2 is a spectrogram of a representative XRD pattern for 2-chloro-4-[[(1R,2R)-2-hydroxy-2-methyl-cyclopentyl]amino]-3-methyl-benzonitrile crystalline Form 2. The XRD spectrogram was obtained as described in the Example 1D below.
Figure 3:
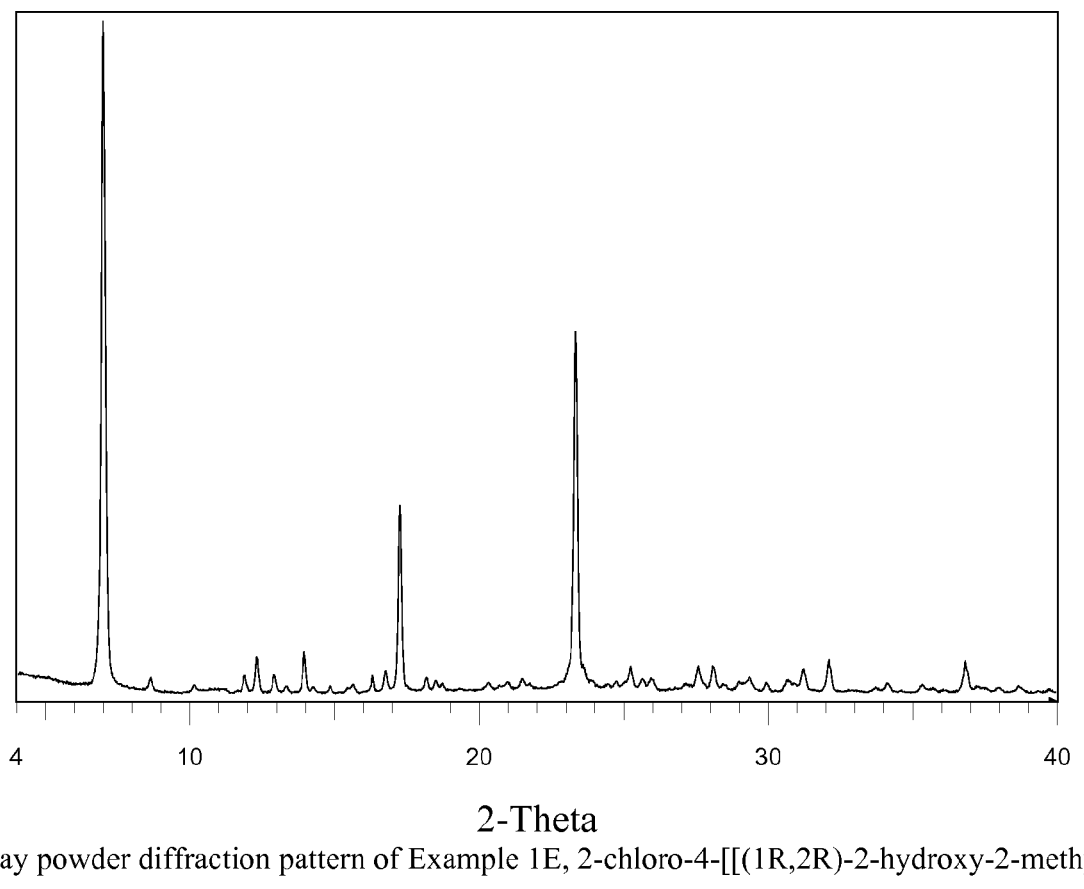
FIG. 3 is a spectrogram of a representative XRD pattern for 2-chloro-4-[[(1R,2R)-2-hydroxy-2-methyl-cyclopentyl]amino]-3-methyl-benzonitrile crystalline ethanol solvate. The XRD spectrogram was obtained as described in the Example 1E below.
Figure 4:
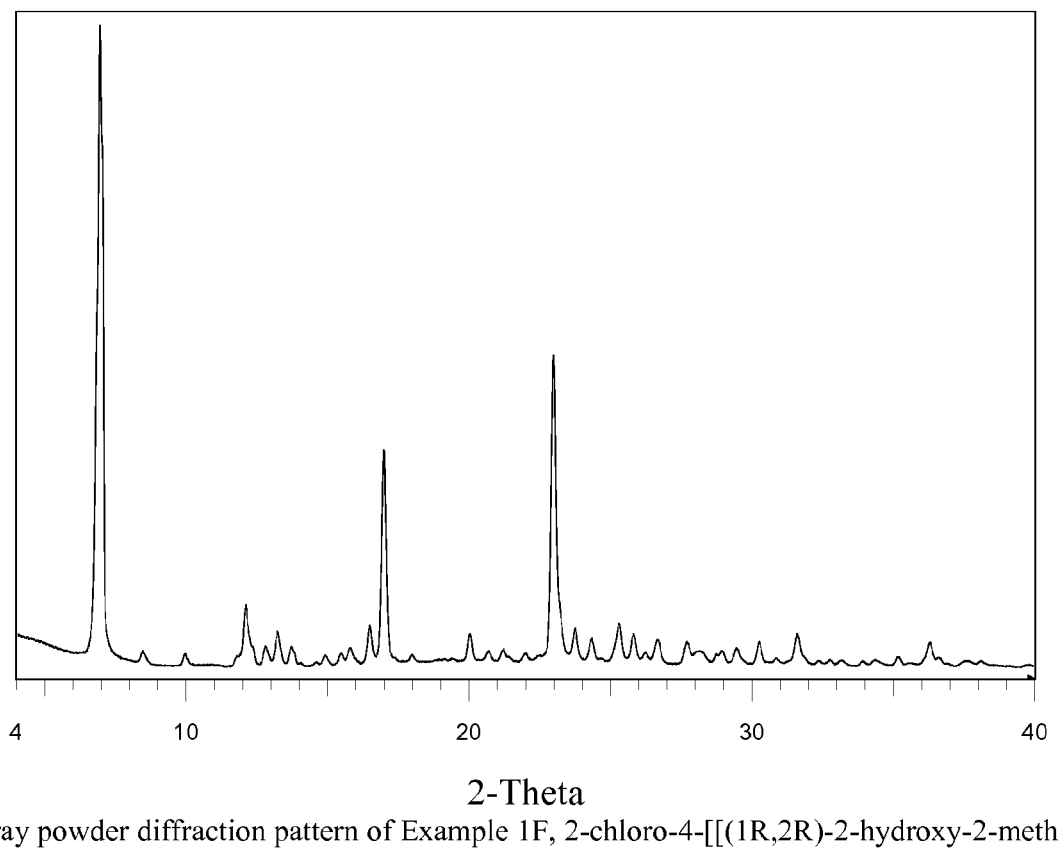
FIG. 4 is a spectrogram of a representative XRD pattern for 2-chloro-4-[[(1R,2R)-2-hydroxy-2-methyl-cyclopentyl]amino]-3-methyl-benzonitrile crystalline isopropanol solvate. The XRD spectrogram was obtained as described in the Example 1F below.

The term "effective amount" is taken to mean the dose or doses of a compound of the invention required to treat muscle atrophy, hypogonadism, or cachexia in a mammal. A compound of the present invention is generally effective over a wide dosage range. For example, dosages per day normally fall within the range of about 0.001 to about 10 mg/kg of body weight. In some instances dosage levels below the lower limit of the aforesaid range may be more than adequate, while in other cases still larger doses may be employed while maintaining a favorable benefit/risk profile, and therefore the above dosage range is not intended to limit the scope of the invention in any way. It will be understood that the amount of a compound actually administered is likely to be determined by a physician, in the light of the relevant circumstances, including the condition to be treated, the chosen route of administration, the actual compound or compounds administered, the age, weight, and response of the individual patient, and the severity of the patient's symptoms.

The term "treating" (or "treat" or "treatment") as used herein refers to prohibiting, restraining, slowing, stopping, or reversing the progression or severity of an existing symptom, condition, or disorder. The term "preventing" (or "prevent" or "prevention") as used herein refers to prohibiting, restraining, or inhibiting the incidence or occurrence of a symptom, condition, or disorder. Symptoms, conditions, or disorders may present as "acute" or "chronic" events. In an acute event compound is administered at the onset of symptom, condition, or disorder and discontinued when the event disappears, whereas a chronic symptom, condition, or disorder is treated throughout the course of the event. The present invention contemplates both acute and chronic treatment.

A compound of the present invention may react with any of a number of inorganic and organic acids to form pharmaceutically acceptable acid addition salts. Pharmaceutically acceptable salts and common methodology for preparing them are well known in the art. See, e.g., P. Stahl, et al. *Handbook of Pharmaceutical Salts: Properties, Selection and Use*, 2$^{nd}$ Revised Edition (Wiley-VCH, 2011); S. M. Berge, et al., "Pharmaceutical Salts," *Journal of Pharmaceutical Sciences*, Vol. 66, No. 1, January 1977.

The skilled artisan will appreciate that the compounds of the invention are comprised of a core that may contain up to three chiral centers, as illustrated in I(a) below:

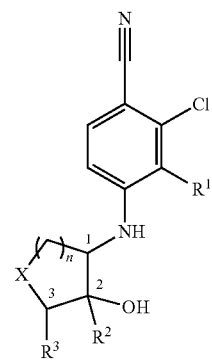

I(a)

Although the present invention contemplates all individual enantiomers, as well as mixtures of the enantiomers of said compounds including racemates, the compounds with the absolute configuration as illustrated in I(b) below are preferred compounds of the invention.

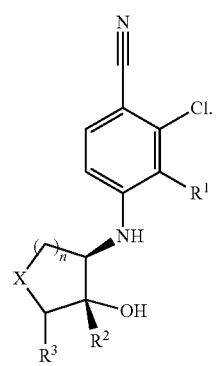

I(b)

Isomers of compounds of the invention are labeled as isomer 1, isomer 2, etc., beginning with the first to elute (lower retention time) from the chromatographic separation method employed and disclosed herein.

The skilled artisan will appreciate that additional chiral centers may be created in the compounds of the invention by the selection of certain variables. The present invention contemplates all individual enantiomers or diastereomers, as well as mixtures of the enantiomers and diastereomers of said compounds including racemates.

The skilled artisan will also appreciate that the Cahn-Ingold-Prelog (R) or (S) designations for all chiral centers will vary depending upon the substitution patterns of the particular compound. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques at any convenient point in the synthesis of compounds of the invention. Single enantiomers and diastereomers of compounds of the invention are a preferred embodiment of the invention.

As a modulator of AR, a compound of the present invention may be useful for treating muscle atrophy. Further, a compound of the present invention may be useful for treating hypogonadism. Even further, a compound of the present invention may be useful for treating cachexia. Another embodiment of the present invention is a compound of the present invention for treating a disease or condition capable of being improved or prevented by modulation of AR. A further embodiment of the present invention is the use of a compound of the present invention for the manufacture of a medicament for treating a disease or condition capable of being improved or prevented by modulation of AR.

A compound of the present invention is preferably formulated as pharmaceutical compositions administered by a variety of routes. Preferably, such compositions are suitable for transdermal delivery and are formulated as a patch, a topical gel, a topical spray, or a topical cream. Such pharmaceutical compositions and processes for preparing same are well known in the art. See, e.g., *Remington: The Science and Practice of Pharmacy* (A. Gennaro, et al., eds., 21st ed., Mack Publishing Co., 2005).

Although all of the exemplified compounds of the invention are androgen receptor agonists, certain classes of compounds are preferred. The following paragraphs describe such preferred classes:

a) n is 1;
b) n is 2;
c) X is —CH$_2$—
d) X is —O—;
e) R$^1$ is —CH$_3$;
f) R$^1$ is —CH$_2$CH$_3$;
g) R$^2$ is —CH$_3$;
h) R$^2$ is H;
i) R$^3$ is —H;
j) R$^3$ is —OH;
k) R$^1$ is —CH$_2$CH$_3$ when R$^3$ is —OH;
l) R$^1$ is —CH$_2$CH$_3$ when X is —O—;
m) R$^1$ is —CH$_3$ when X is —CH$_2$—;
n) the compound of the present invention is the free base;
o) the compound of the present invention is the ethanol solvate;
p) the compound of the present invention is the isopropanol solvate.

A preferred embodiment of the compounds of the present invention relates to compounds of the invention of the following formula,

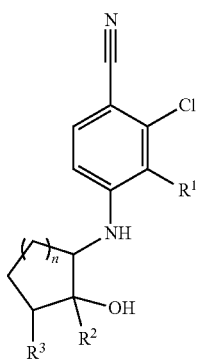

wherein
n is 1 or 2;
R$^1$ is —CH$_3$ or —CH$_2$CH$_3$;
R$^2$ is —H or —CH$_3$;
R$^3$ is —H or —OH;
or a pharmaceutically acceptable salt thereof.

Another preferred embodiment of the compounds of the present invention relates to compounds of the invention of the following formula,

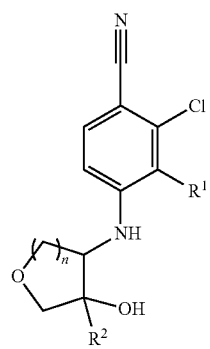

wherein
n is 1 or 2;
R$^1$ is —CH$_3$ or —CH$_2$CH$_3$;
R$^2$ is —H or —CH$_3$;
or a pharmaceutically acceptable salt thereof A further preferred embodiment of the compounds of the present invention relates to compounds of the following formula,

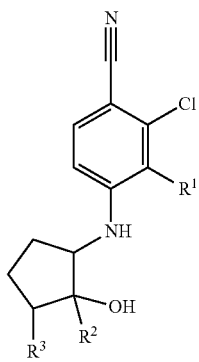

wherein
R$^1$ is —CH$_3$ or —CH$_2$CH$_3$;
R$^2$ is —H or —CH$_3$;
R$^3$ is —H or —OH;
or a pharmaceutically acceptable salt thereof. In said embodiment, it is preferred that R$^1$ is —CH$_3$. It is also preferred in said embodiment that R$^1$ is —CH$_2$CH$_3$ when R$^3$ is —OH.

Another further preferred embodiment of the compounds of the present invention relates to compounds of the following formula,

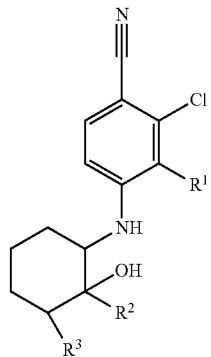

wherein

R¹ is —CH₃ or —CH₂CH₃;
R² is —H or —CH₃;
R³ is —H or —OH;

or a pharmaceutically acceptable salt thereof. In said embodiment, it is preferred that R¹ is —CH₃. It is also preferred in said embodiment that R¹ is —CH₂CH₃ when R³ is —OH.

Another preferred embodiment of the compounds of the present invention relates to compounds of the following formula,

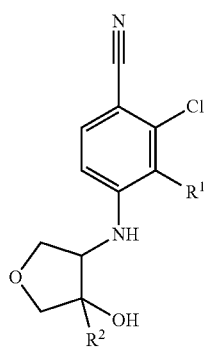

wherein

R¹ is —CH₃ or —CH₂CH₃;
R² is —H or —CH₃;

or a pharmaceutically acceptable salt thereof. In said embodiment, it is preferred that R¹ is —CH₂CH₃.

A further preferred embodiment of the compounds of the present invention relates to compounds of the following formula,

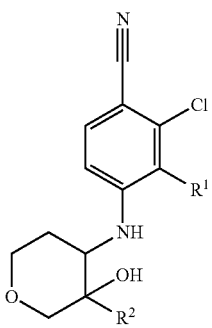

wherein

R¹ is —CH₃ or —CH₂CH₃;
R² is —H or —CH₃;

or a pharmaceutically acceptable salt thereof. In said embodiment, it is preferred that R¹ is —CH₂CH₃.

Another further preferred embodiment of the present invention relates to compounds of the following formula:

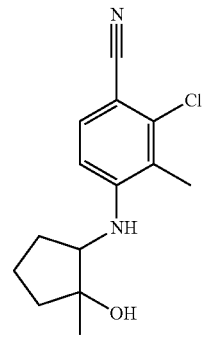 [SMILES: Cc1c(NC2CCCC2(C)O)ccc(C#N)c1Cl]

or a pharmaceutically acceptable salt thereof.
An especially preferred embodiment of the present invention relates to the compound, 2-chloro-4-[[(1R,2R)-2-hydroxy-2-methyl-cyclopentyl]amino]-3-methyl-benzonitrile

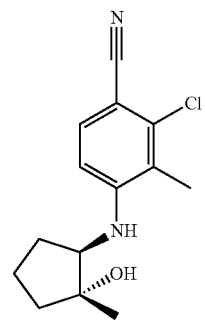 [SMILES: Cc1c(N[C@@H]2CCC[C@@]2(C)O)ccc(C#N)c1Cl]

or a pharmaceutically acceptable salt thereof.
Another especially preferred embodiment of the present invention relates to the compound, 2-chloro-4-[[(1S,2R)-2-hydroxy-2-methyl-cyclopentyl]amino]-3-methyl-benzonitrile,

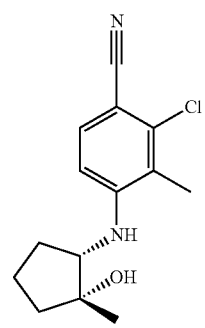 [SMILES: Cc1c(N[C@H]2CCC[C@@]2(C)O)ccc(C#N)c1Cl]

or a pharmaceutically acceptable salt thereof.

As used herein, the following terms have the meanings indicated: "abs" refers to absolute; "CMV promoter" refers to cytomegalovirus promoter; "Bn" refers to benzyl; "BOC" refers to tert-butoxycarbonyl; "CS-FBS" refers to charcoal stripped fetal bovine serum; "DMAC" refers to dimethylacetamide; "DMEM" refers to Dulbecco's Modified Eagle Medium; "DMF" refers to dimethylformamide "DMSO" refers to dimethyl sulfoxide; DTT" refers to dithiothreitol;

"EDTA" refers to ethylenediaminetetraacetic acid; "EtOAc" refers to ethyl acetate; "EtOH" refers to ethanol; "Ex" refers to Example; "FBS" refers to fetal bovine serum; "h" refers to hours; "HEK" refers to human embryonic kidney; "HEPES" refers to 4-(2-hydroxyethyl)-1-piperazineethanesulfonic acid; "IPM" refers to isopropyl myristate; "LDA" refers to lithium diisopropyl amide; "MCPBA" refers to meta-chloroperoxybenzoic acid; "MeOH" refers to methanol; "MTBE" refers to methyl tert-butyl ether; "min" refers to minutes; "NCS" refers to N-chlorosuccinimide; "Prep" refers to Preparation; "rel" refers to relative; "SFC" refers to super-critical fluid chromatography; "TBAF" refers to tetra-butylammonium fluoride; "TBDMS" refers to t-butyldimethylsilyl; "TBDPS" refers to t-butyldiphenylsilyl; "TEA" refers to triethylamine; "TEMPO" refers to 2,2,6,6-tetramethylpiperidine-N-oxide; "THF" refers to tetrahydrofuran; "TMS" refers to trimethylsilyl; "TK promoter" refers to thymidine kinase promoter; and "XRD" refers to x-ray diffraction.

In the schemes below, all substituents unless otherwise indicated, are as previously defined. The reagents and starting materials are generally readily available to one of ordinary skill in the art. Others may be made by standard techniques of organic and heterocyclic chemistry which are analogous to the syntheses of known structurally-similar compounds and the procedures described in the Preparations and Examples which follow including any novel procedures.

The compounds of the present invention comprise up to three chiral centers or more. It will be recognized by one skilled in the art that there are common techniques useful for separating and identifying diastereomers or enantiomers. Such techniques include silica gel chromatography to separate diastereomers, chiral chromatography to separate enantiomers, synthesis using starting materials of known configuration, or making use of synthetic techniques which are known to provide defined stereochemistry at a chiral center, or one relative diastereomeric configuration, such as cis or trans.

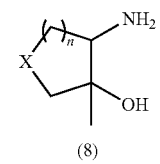

(8)

Scheme 1 depicts formation of amino alcohols of formula (8).

In Step A, a cyclic olefin of formula (1) is oxidized to an epoxide of formula (2). The olefin (1) is treated with an oxidizing agent, such as MCPBA, in an inert solvent, such as dichloromethane at 0 to 40° C. for 2 to 24 h to obtain the epoxide (2).

In Step B, an epoxide of formula (2) is opened to provide the azido-alcohol of formula (3). The reaction proceeds in a solvent mixture of water and MeOH using an azide source, such as sodium azide, in the presence of ammonium chloride at a temperature of 50 to 70° C. for a period of 2 to 24 h. Alternatively, the reaction can be performed in a solvent such as DMF, with or without the addition of a Lewis acid, such as lithium perchlorate, at 50 to 100° C., preferably at about 90° C. for 12 to 72 h.

In Step C, the azide (3) is reduced to the amine of formula (4), which can be reacted directly with a fluoro-benzonitrile (Scheme 5). The amine (4) can be obtained by hydrogenation over a palladium catalyst, such as 10% palladium on carbon, in an inert solvent, such as MeOH or EtOH at about 10 to 40° C.

Alternatively, in Step B$^1$, wherein R$^2$ is methyl, the amine (4) can be obtained directly from the epoxide (2) by reaction with ammonium hydroxide. The reaction proceeds in a pressure vessel, in a solvent mixture of water/EtOH at 70 to 100° C. for about 2 to 18 h.

Regarding the amine of formula (4), wherein R$^2$=H, the methyl group can be introduced using Steps D-G. Protection of the amine (4) with a BOC group in Step D gives a protected amino-alcohol of formula (5). Preferred conditions for protection of the amine use di-tert-butyldicarbonate in a solvent mixture of acetone and water, in the presence of an inorganic base such NaHCO$_3$.

In Scheme 1 Step E, the protected amino-alcohol (5) is oxidized to the ketone (6). The skilled artisan will recognize there are many methods to effect such an oxidation. Preferred conditions use the well-known Swern oxidation. Thus, oxalyl chloride and DMSO are combined in an inert solvent, such as dichloromethane or THF, at a temperature of −80 to −60° C. and allowed to react at that temperature for a period of about 5 to 20 min to produce the reactive intermediate dimethylchlorosulfonium chloride. This is followed by addition of the alcohol (5), again at a temperature of −80 to −60° C. with reaction for a period of about 30 to 60 min. Finally, an organic base, such as TEA is added at the same temperature. At least 2 eq of the base is added, typically about 5 to 6 eq of TEA, and the reaction allowed to warm to room temperature over 1 to 24 h.

Alternatively, the alcohol (5) can be oxidized using Anelli's conditions wherein TEMPO is used catalytically, at a catalyst load of about 5 mol %, in the presence of potassium bromide, in a biphasic solvent system of dichloromethane and aqueous sodium hypochlorite, wherein potassium carbonate or other inorganic base is added to adjust the sodium hypochlorite solution to about pH=7.5-8. The TEMPO plus the alcohol (5) in dichloromethane are cooled to a temperature of −5 to 5° C. The temperature is maintained during the Scheme 1

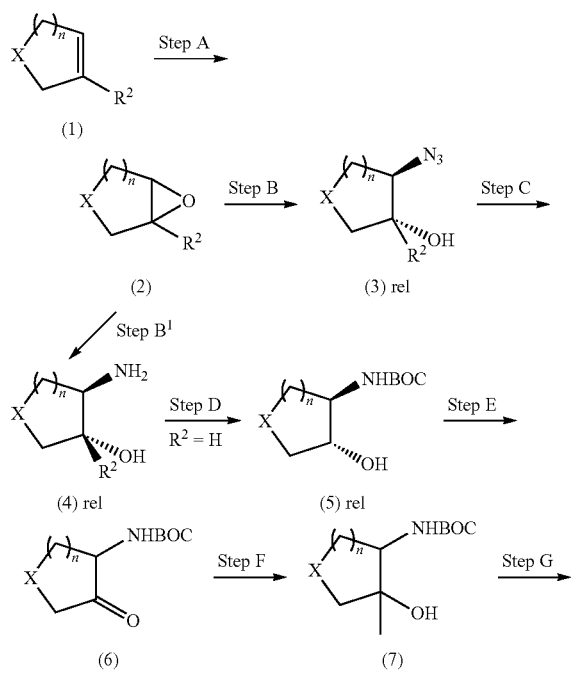

addition of the pH adjusted sodium hypochlorite solution and through the remainder of the reaction which proceeds for about 20 min to 4 h to provide the ketone (6).

In Step F, the ketone (6) undergoes a Grignard reaction with methylmagnesium bromide to provide the tertiary alcohol of formula (7). The reaction proceeds in an inert solvent such as diethyl ether or THF. The Grignard reagent, methylmagnesium bromide, is added slowly at a temperature of −80 to 5° C., preferably at a temperature of −5 to 5° C., and the reaction allowed to warm to room temperature over 12 to 48 h.

In Step G, the BOC protecting group is removed to give the unprotected amine of formula (8). Acidic conditions for removal of boc groups, such as HCl in dioxane, are well known in the art.

Different protecting groups can be employed by one skilled in the art. For Example, the amine of formula (4) can be protected by bis-alkylation with benzyl bromide in a solvent system, such as acetone/water, in the presence of an inorganic base, such as potassium carbonate and heated at 40° C. to the reflux temperature of the solvent to provide the dibenzylamino analog. Oxidation to the ketone and subsequent reaction with methylmagnesium bromide can provide the tertiary amino-alcohol. The benzyl groups can be removed using hydrogenation with Pd catalysts common in the art, such as palladium black or palladium hydroxide on carbon.

One skilled in the art will recognize that some of the amines (4) are commercially available as pure stereoisomers, such as (1R,2S)-2-aminocyclopentanol, thus obviating the need for Steps A-C.

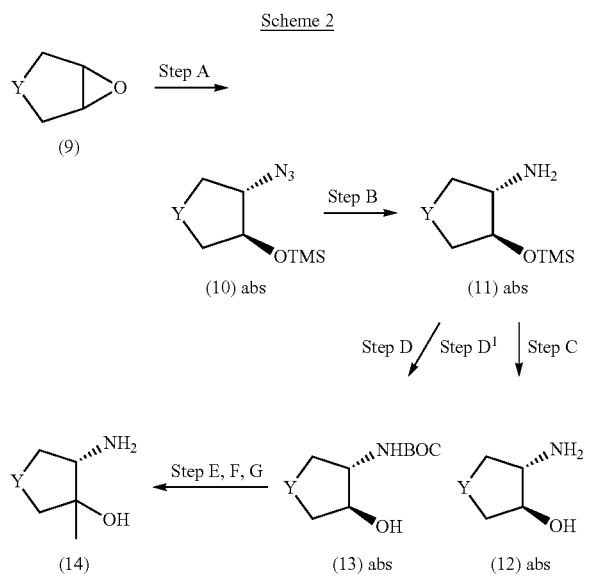

Scheme 2 depicts formation of amino alcohols of formula (12) and (14), wherein chirality is introduced using Jacobsen chemistry starting with a meso epoxide of formula (9) (wherein Y=CH$_2$, CH$_2$CH$_2$, or O).

For example, in Step A, a meso epoxide (9) undergoes an asymmetric ring opening with azidotrimethylsilane using a chiral (salen)Cr(II) complex or a chiral (salen)Co(II) complex, such as (1R,2R)-(−)-1,2-cyclohexanediamino-N,N'-bis(3,5-di-t-butylsalicylidene)cobalt (II) (see Jacobsen, E. N, et al J. Org. Chem. 1997, 62, 4197-4199). The reaction is run neat at room temperature to 60° C. for 4 to 24 h.

In Step B, the azide (10) is reduced to the amine of formula (11), as previously described for Scheme 1, Step C. This can be followed by removal of the TMS group using fluoride anion, such as with TBAF to provide a chiral amino-alcohol (12).

If it is desired to insert the methyl group, then further protection group manipulation can be done with the amine protected with a BOC group (Step D), removal of TMS (Step D$^1$) and then elaboration to the amino-alcohol of formula (14) following Steps E, F, and G which are exactly analogous to Steps E, F, and G in Scheme 1.

Use of the other chiral salen complex, for example (1S, 2S)-(−)-1,2-cyclohexanediamino-N,N'-bis(3,5-di-t-butylsalicylidene)cobalt (II) gives access to molecules with stereochemistry opposite to that shown for intermediates (10) to (14). After attachment to the benzonitrile (Scheme 5) the diastereomers (amino and hydroxyl groups cis and trans) can be conveniently separated using silica gel chromatography.

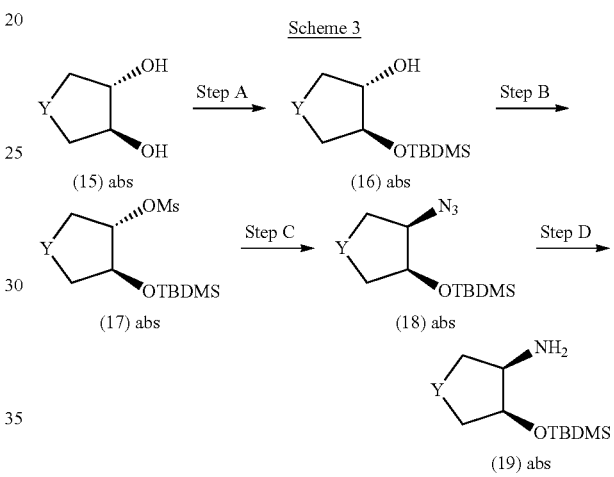

Scheme 3 depicts formation of cis-amino alcohols of formula (19), starting with a chiral diol of formula (15) (wherein Y=CH$_2$ or O).

In Step A, the diol (15) is reacted with TBDMSCl (1.1 eq) in an inert solvent, such as dichloromethane, in the presence of an organic base, such as TEA at room temperature for 2 to 5 days to give the silyloxy-hydroxy (16).

In Step B, the other hydroxyl group of (16) is mesylated using standard conditions to give the mesylate (17). The reaction proceeds in an inert solvent, such as dichloromethane, in the presence of 2,6-lutidine and an organic base such as triethylamine or diisopropylethylamine using methanesulfonyl chloride. The reaction is performed at −20° C. to room temperature for 4 to 24 h.

In Scheme 3, Step C, the mesylate (17) undergoes an S$_N$2 displacement with sodium azide to give the silyloxy azide of formula (18) wherein the stereochemistry at the reacting carbon atom has been inverted. The reaction proceeds in an inert solvent, such as DMF at 60 to 130° C. for 2 days to 2 weeks. A phase transfer catalyst can be added, such as tetrabutylammonium iodide.

In Step D, the silyloxy azide (18) is reduced to the silyloxy amine (19) using conditions as previously described for Scheme 1, Step C.

Using the enantiomer of diol (15) gives access to the other cis enantiomer.

Scheme 4

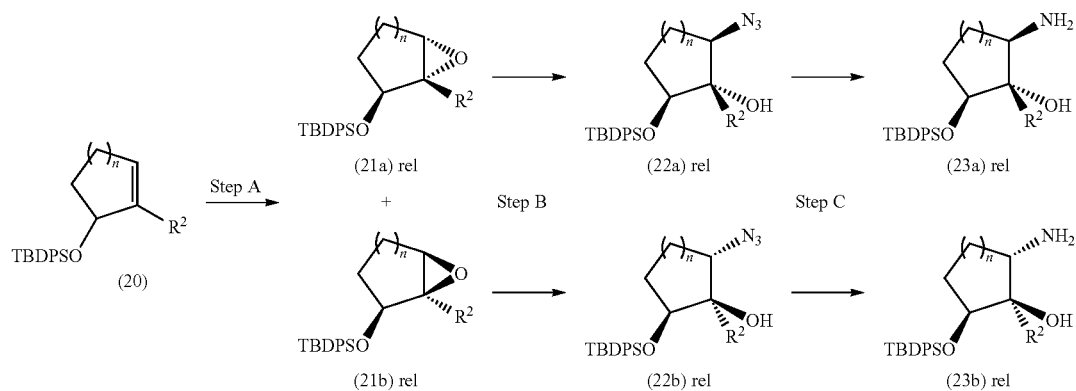

Scheme 4 depicts formation of cyclopentyl and cyclohexylamino diols of formula (23a) and (23b).

In Step A, the olefin of formula (20) is oxidized to the epoxides (21a) and (21b) using MCPBA. The reaction is carried out in a biphasic solvent system of dichloromethane and aqueous sodium bicarbonate at 0° C. to room temperature for 4 to 24 h. Additional MCPBA and aqueous sodium bicarbonate can be added if needed. The diastereomeric epoxides are separated by chromatography and carried forward separately in Steps B and C.

In Step B, the epoxides (21a) or (21b) are opened with sodium azide to give the azido-alcohols (22a) and (22b) as previously described for Scheme 1, Step B.

Step C, reduction of the azide (22a) or (22b) is analogous to Scheme 1, Step C to provide the amino-alcohols (23a) or (23b).

ment can be done with benzylamine followed by benzylation of the benzyl allylic amine with benzyl bromide. Alternatively, the dibenzyl allylic amine (24) could be obtained directly by reductive amination on the corresponding ketone with dibenzylamine or benzylamine, followed by benzylation with benzylbromide. The dibenzyl allylic amine of formula (24), wherein $R^2$=Me, can be obtained by treating 2-methyl-2-cyclopenten-1-ol or 2-methyl-2-cyclohexene-1-ol with NCS and dimethylsulfide to give 5-chloro-1-methyl-cyclopentene or the corresponding cyclohexene (see Funk, R. L. et al *Tetrahedron* 1985, 41, 3479-3495, compound 46b). The same displacement chemistry is applied as described previously. One skilled in the art will recognize that the chloride could also be obtained by treating the alcohol with thionyl chloride.

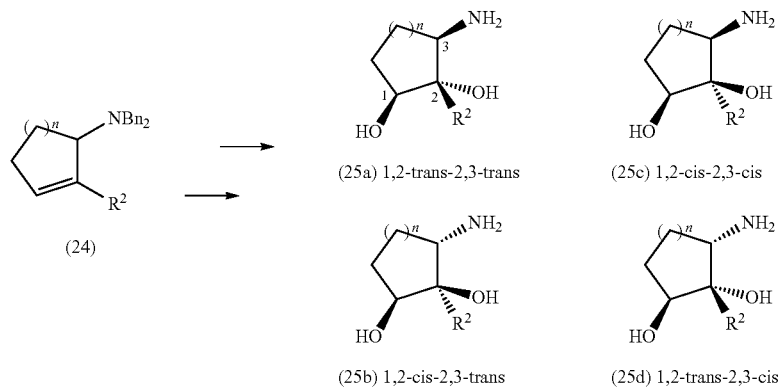

(25a) 1,2-trans-2,3-trans (25c) 1,2-cis-2,3-cis (24)

(25b) 1,2-cis-2,3-trans (25d) 1,2-trans-2,3-cis

Depicted in Scheme 4A is an alternative method for obtaining all four diastereomers of amino-diols of formula (25a-d) using chemistry of Davies (see Aciro, C. et al *Org. Biomol. Chem.* 2008, 6, 3751-3761; Aciro, C. et al *Org. Biomol. Chem.* 2008, 6, 3762-3770; Bond, C. W. et al *J. Org. Chem.* 2009, 74, 6735-6748), particularly those of (25c) and (25d) wherein the amine and the adjacent hydroxyl are cis to each other.

Dibenzyl allylic amine (24) can be obtained from cyclohexene by bromination, followed by bromide displacement with dibenzylamine (see Davies). Alternatively, the displacement The skilled artisan will recognize that there are yet other methodologies available in the literature that can be applied to obtain the diastereomers (25a-d). For example, starting with the analogous acetamide (rather than the dibenzylamine), Whitten and coworkers (see Whitten, J. P., McCarthy, J. R., and Whalon, M. R. *J. Org. Chem.* 1985, 50, 4399-4402) obtained all four diasteromers (wherein n=1, $R^2$=H). Furthermore, Donohoe and coworkers (Blades, K., Donohoe, T. J., Winter, J. J. G., and Stemp, G. *Tetrahedron Lett.,* 2000, 41, 4701-4704), using the analogous allylic trichloroacetamide, accomplished syn selectivity using catalytic osmium tetroxide in the presence of quinuclidine-N-oxide.

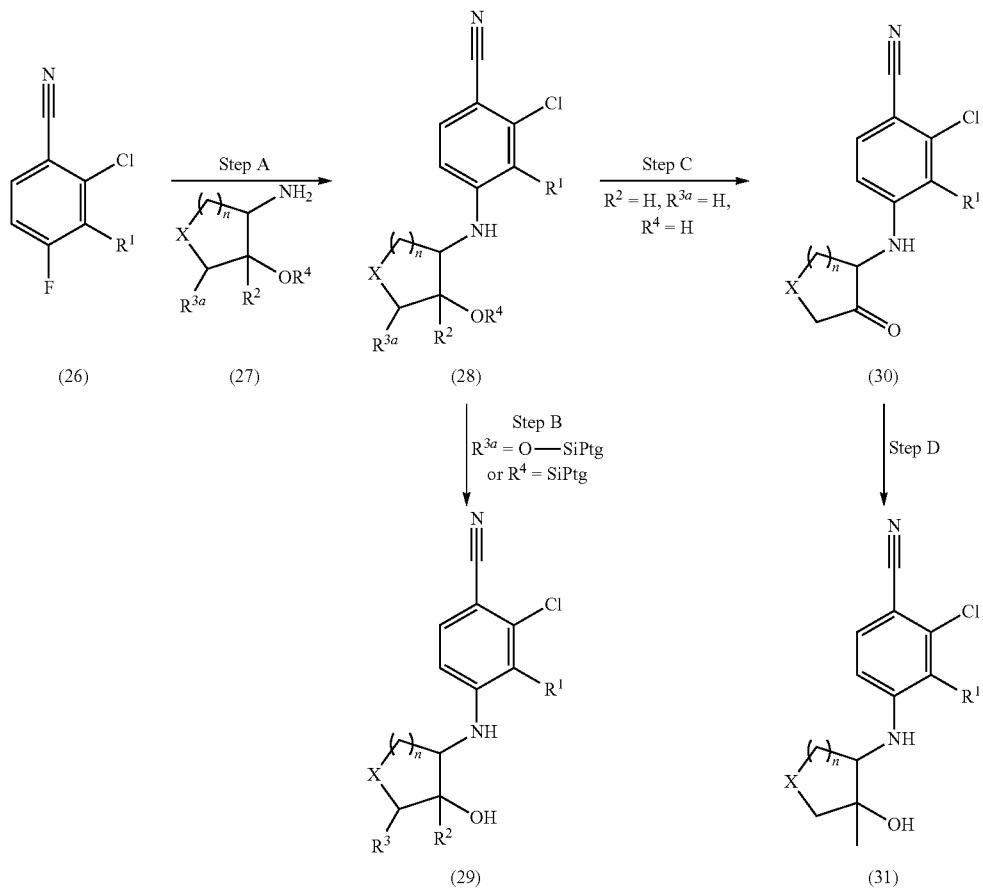

Scheme 5 shows formation of compounds of the invention, amino benzonitriles of formula (29) and (31) (stereochemistry not shown; $R^{3a}$ is H or if $X=CH_2$, $R^{3a}$ can also be OTBDPS; $R^4$=H or TBDMS).

In Step A, a fluoro-benzonitrile of formula (26) undergoes a nucleophilic aromatic substitution with an amine of formula (27), whose synthesis is described in Schemes 1-4a. The reaction proceeds in an inert solvent such as DMF, DMAC, or DMSO, preferably in a solvent mixture of DMSO/water in a ratio of 7/1 to 10/1, in the presence of an inorganic base, preferably lithium carbonate, but also sodium carbonate. The reaction is carried out in a pressure vessel at 100 to 150° C., preferably about 130° C. for 16 to 48 h. Alternatively, the reaction can be successfully effected using microwave radiation, using simply an organic base, such as diisopropylethylamine without additional solvent, at a temperature of 170 to 190° C., preferably at 180° C., to provide an amino benzonitrile of formula (28).

In Step B, amino benzonitriles (28) which contain a silyl protecting group ($R^{3a}$ or $R^4$) are deprotected using fluoride anion, such as with TBAF, as described for Scheme 2, Step C.

If desired, compounds of formula (28), wherein $R^2=R^4$=H can be further elaborated to compounds (31) (wherein $R^2=CH_3$) using Steps C and D. In Step C, the hydroxyl of the amino benzonitrile (28) is oxidized to the α-keto amino benzonitrile (30) using Swern conditions as described previously for Scheme 1, Step E.

In Step D, the α-keto amino benzonitrile (30) undergoes a Grignard reaction with methylmagnesium bromide to give the α-methyl-α-hydroxy amino benzonitrile of formula (31).

The reaction proceeds in an inert solvent, such as THF, at 0° C. to room temperature, for a period of 15 min-24 h.

The 2-chloro-3-alkyl-4-fluoro-benzonitrile of formula (26), wherein $R^1=CH_3$ or $CH_2CH_3$, is synthesized in one step from 2-chloro-4-fluoro-benzonitrile using a strong organic base such as LDA, which can be generated in situ using diisopropylamine and n-butyllithium. The LDA is added dropwise to the benzonitrile in a solvent such as THF, at a temperature of −80 to −60° C., preferably at −70° C., for a period of 4 to 20 h. Iodomethane or iodoethane are added at the same temperature, over about 2 to 3 h, and the temperature allowed to raise to −10 to 5° C. for about 12 to 24 h.

Diastereomers or enantiomers of the amino benzonitriles (29) and (31) can be separated by techniques such as silica gel chromatography or chiral chromatography.

PREPARATIONS AND EXAMPLES

The following Preparations and Examples further illustrate the invention and represent a typical synthesis of the compound of the invention. The reagents and starting materials are readily available or may be readily synthesized by one of ordinary skill in the art. It should be understood that the Preparations and Examples are set forth by way of illustration and not limitation, and that various modifications may be made by one of ordinary skill in the art.

The naming of the following Preparations and Examples is generally done using the IUPAC naming feature in SYMYX® Draw version 3.2.NET.

Drawings wherein the absolute stereochemistry is known are labeled "absolute." Drawings wherein only the cis or trans relationship between the amino and hydroxyl groups is known are labeled "relative" and the corresponding drawing indicating the relative stereochemistry using wedged bonds. Regarding stereochemical designation, the diastereomeric relationship on the monocyclic ring is generally indicated using the cis/trans nomenclature. The diastereomeric relationship on those few compounds which have three chiral centers on the monocyclic ring are designated, for example, by rel-(1R,2S,3S), indicating that the (1R,2S,3S) isomer and the (1S,2R,3R) isomer are both present in the diastereomeric mixture.

Preparation 1

2-Chloro-4-fluoro-3-methyl-benzonitrile

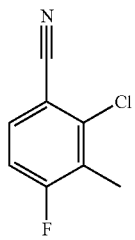

To a solution of diisopropylamine (474 mL, 3.35 mol) in anhydrous THF (5.8 L) at −5° C. under a nitrogen atmosphere is added dropwise 2.5 M n-butyllithium in hexanes (1.24 L, 3.10 mol) over 3 h and the resulting mixture is stirred at −5° C. for one additional hour. The LDA solution is added dropwise to a solution of 2-chloro-4-fluoro-benzonitrile (400 g, 2.58 mol) in anhydrous THF (5.8 L) at −70° C. over 6 h and then stirred at −70° C. overnight. Iodomethane (643 mL, 10.32 mol) is added dropwise over 2.5 h and the temperature is raised to −5° C. for 17 h. Saturated aqueous ammonium chloride (3 L) is added. The solution is diluted with water (3.5 L) and extracted with diethyl ether (2×2 L). The organic phases are separated, combined, dried over anhydrous sodium sulfate, filtered, and concentrated to afford a black solid. The solid is purified through a silica gel pad eluting with EtOAc/hexanes (1/40) to obtain the title compound (323 g, 74%). $^1$H NMR (300 MHz, CDCl$_3$) δ 7.08 (dd, J=8.6, 8.6 Hz, 1H), 7.54 (dd, J=8.6, 5.6 Hz, 1H), 2.36 (d, J=2.4 Hz, 3H).

Preparation 2

2-chloro-3-ethyl-4-fluoro-benzonitrile

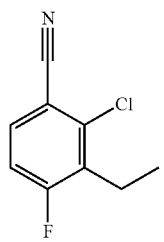

The title compound is prepared by essentially following the procedure described in Preparation 1, using 2-chloro-4-fluoro-benzonitrile (12.2 g, 78.4 mmol), and iodoethane (18.4 g, 9.43 mL, 118 mmol). The crude product is purified on silica gel using 15-50% dichloromethane/hexanes to give the title compound as shiny white crystals (4.06 g, 28%). $^1$H-NMR (400 MHz, CDCl$_3$) δ 7.54 (dd, J=5.6, 8.6 Hz, 1H), 7.07 (t, J=8.6 Hz, 1H), 2.85 (qd, J=7.5, 2.3 Hz, 2H), 1.19 (t, J=7.5 Hz, 3H).

Preparation 3

1-methyl-6-oxabicyclo[3.1.0]hexane

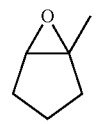

A solution of 1-methylcyclopentene (25 mL, 0.24 mol) in dichloromethane (770 mL) is cooled to 5° C. under nitrogen. MCPBA (87.5 g, 0.36 mol, 1.5 eq, 71% wt) is added in portions and the mixture is stirred at room temperature overnight. The reaction mixture is filtered through a pad of diatomaceous earth. The filtrate is washed with aqueous saturated sodium bicarbonate (500 mL) and 10% aqueous sodium thiosulfate (100 mL). The organic portion is concentrated under reduced pressure while keeping the water bath temperature below 20° C. to obtain the title compound (24 g, 99%). $^1$H NMR (400 MHz, CDCl$_3$) δ 3.42 (s, 1H), 1.81-1.99 (m, 2H), 1.38-1.65 (m, 4H), 1.42 (s, 3H). GC-MS m/z 98 (M$^+$).

Preparation 4 trans-2-Amino-1-methyl-cyclopentanol

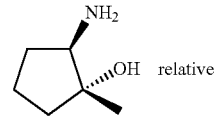

In a glass pressure vessel, a solution of 1-methyl-6-oxabicyclo[3.1.0]hexane (25 g, 0.25 mol), ammonium hydroxide (50 mL, 0.36 mmol), water (50 mL), and ethanol (100 mL) is heated at 90° C. for 4 h. The reaction mixture is concentrated and the residue is coevaporated twice with isopropanol (100 mL) to obtain the title compound (28.4 g) that is up to 45% pure by NMR. GC-MS m/z 115 (M$^+$). The crude material is used in the next step (Example 1) without additional purification.

Preparation 5

(1R,2S)-2-(Dibenzylamino)cyclopentanol

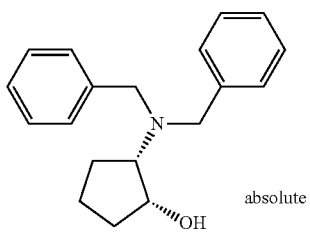 [SMILES: O[C@@H]1CCC[C@@H]1N(Cc1ccccc1)Cc1ccccc1]

To a solution of (1R,2S)-2-aminocyclopentanol hydrochloride (9.3 g, 67.6 mmol) and potassium carbonate (28.02 g, 203 mmol) in acetone (675 mL) and water (48 mL) is added benzyl bromide (16.1 mL, 135 mmol) in a single portion and the mixture refluxed overnight. The heat is removed and the reaction is concentrated under reduced pressure. The residue is diluted with aqueous 1 M HCl and washed with ether. The aqueous layer is made alkaline with sodium hydroxide and extracted with EtOAc. The organic portion is dried over sodium sulfate, filtered, and concentrated under reduced pressure to afford the title compound as a yellow oil (16.98 g, 89%). ES/MS m/z 282 (M+1).

Preparation 6

(2S)-2-(Dibenzylamino)cyclopentanone

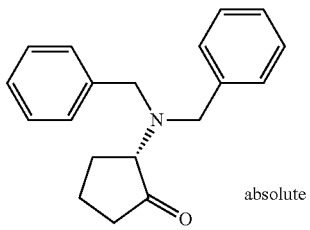 [SMILES: O=C1CCC[C@@H]1N(Cc1ccccc1)Cc1ccccc1]

absolute

To a solution of oxalyl chloride (6.28 mL, 72.4 mmol) in dichloromethane (75 mL) at −60° C. under nitrogen is added a solution of DMSO (10.7 mL, 151 mmol) in dichloromethane (75 mL) dropwise and stirred at −60° C. for 15 min. (1R,2S)-2-(dibenzylamino)cyclopentanol (17.0 g, 60 mmol) in dichloromethane (75 mL) is added and the reaction is stirred at −60° C. for 30 min. TEA (46 mL, 330 mmol) is added and the reaction is allowed to warm to room temperature and stirred for 1 h. Water is added (100 mL) and the reaction is stirred overnight. The dichloromethane layer is separated, dried over anhydrous sodium sulfate, filtered, and concentrated under reduced pressure to afford the title compound as an orange oil (13.96 g, 83%). ES/MS m/z 280 (M+1).

Preparation 7

(1R,2S)-2-(Dibenzylamino)-1-methyl-cyclopentanol (enantioenriched)

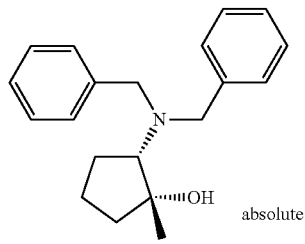 [SMILES: C[C@@]1(O)CCC[C@@H]1N(Cc1ccccc1)Cc1ccccc1]

absolute

To a solution of (2S)-2-(dibenzylamino)cyclopentanone (8.31 g, 29.7 mmol) in diethyl ether (149 mL) at −78° C. is added methyl magnesium bromide (29.7 mL, 89.1 mmol, 3 M in diethyl ether) slowly. The mixture is stirred at −78° C. for 4 h and then the reaction is allowed to warm to room temperature. Water is added to the reaction, resulting in an emulsion. Aqueous 1 M hydrochloric acid is added to break up the emulsion while keeping the aqueous phase basic. The aqueous phase is extracted twice with EtOAc. The combined organic portions are dried over sodium sulfate, filtered, and concentrated under reduced pressure. The resulting residue is purified by silica gel chromatography (10% EtOAc/hexanes) to obtain the product. The material is dissolved in 1 M hydrochloric acid and extracted four times with EtOAc. The combined organic layers are dried over sodium sulfate, filtered, and concentrated under reduced pressure to afford the title compound as an orange solid (3.49 g, 40%). ES/MS m/z 296 (M+1).

Preparation 8

(1R,2S)-2-Amino-1-methyl-cyclopentanol (enantioenriched)

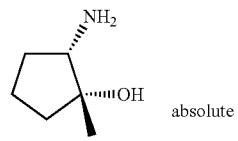

absolute

Palladium black (1.617 g), MeOH (150 mL), and (1R,2S)-2-(dibenzylamino)-1-methyl-cyclopentanol (3.49 g, 11.8 mmol) are combined in a Parr bottle and hydrogenated at room temperature overnight at 50-60 psi. No change is observed by ES/MS and additional palladium black (0.51 g) is added and the hydrogenation continued for 6 h at 30° C./60 psi. There is no apparent change. The reaction is filtered and resubmitted to hydrogenation with fresh palladium black (1.04 g) in MeOH. After 20 h, ES/MS still shows starting material with no product observed. The mixture was filtered and concentrated. The material is resubmitted to hydrogenation in MeOH (100 mL) using palladium black (1.02 g) for 24 h at 30° C./60 psi. There is no change in the progress of the reaction. The hydrogenation is continued, heating at 60° C. at 45-60 psi for about 52 h. Starting material is still present by GC-MS. The mixture is filtered and concentrated. The resulting material is resubmitted to hydrogenation using palladium black (1.57 g) in MeOH (100 mL) at 30° C./60 psi for 24 h. ES/MS provides evidence of removal of one benzyl group with a small amount of starting material still present. 20% Palladium hydroxide on carbon (0.41 g) is added and the hydrogenation is continued at 30° C./60 psi for 20 h. ES/MS shows no starting material, but also no product peak is observed. The reaction mixture is filtered and concentrated. The resulting material is resubmitted to hydrogenation using fresh palladium black (1.20 g) in MeOH (100 mL) at 30° C./60 psi for 23 h. ES/MS still shows no formation of product. The hydrogenation is continued with heating at 40° C. for 24 h. There is no change by ES/MS. 20% Palladium hydroxide on carbon (2.05 g) is added and the hydrogenation is continued at room temperature/60 psi for 67 h. The reaction is filtered and concentrated down. (A small aliquot (74 mg) is hydrogenated with ruthenium (IV) oxide (104 mg) in t-butanol (25 mL) at 60° C./60 psi overnight. This results in reduction of the benzene ring without deprotection as shown by ES/MS.) The resulting material is resubmitted to hydrogenation using 20% palladium hydroxide on carbon (1.01 g) in MeOH (100 mL) at 40° C./50-60 psi for 21 h. On ES/MS there is a small amount of product at 116 (M+1) and a significant peak at 206 (M+1) for mono-benzylated intermediate. Palladium black (1.01 g) is added and the hydrogenation continued at 30° C./60 psi for 23 h. ES/MS does not show any starting material or intermediate with peak 116 (M+1) and a potential impurity at 158. The reaction mixture is filtered through diatomaceous earth and concentrated under reduced pressure to obtain the crude title compound as a tan oil (1.61 g, quantitative). The material is used without further purification in the next step (Example 2) and is later found to be partially racemized. ES/MS m/z 116 (M+1). $^1$H NMR (400 MHz, DMSO-$d_6$) δ 7.84-7.85 (m, 1H), 5.11 (s, 1H), 3.03-3.05 (m, 1H), 1.92-1.94 (m, 1H), 1.75-1.76 (m, 1H), 1.49-1.51 (m, 1H), 1.21 (s, 3H).

Alternate Preparation 1 of
2-amino-1-methyl-cyclopentanol

Preparations 9-12

Preparation 9 trans-tert-Butyl
N-[-2-hydroxycyclopentyl]carbamate

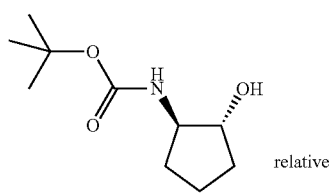

relative

To a solution of trans-2-aminocyclopentanol hydrochloride (100 g, 726.7 mmol), in MeOH (1.45 L) at room temperature under nitrogen, is added sodium carbonate (77 g, 726.7 mmol) and di-tert-butyl dicarbonate (182 mL, 835.7 mmol). The mixture is stirred overnight. The mixture is filtered over a paper filter and methanol is evaporated. The resulting residue is diluted with water and stirred for 30 min to give an off-white solid which is collected by filtration. The solid is dried under vacuum to yield the title compound as a pale cream solid (172.4 g, 89%). $^1$H-NMR (300 MHz, DMSO-$d_6$) δ 6.72 (d, 1H, NH), 4.61 (br s, 1H), 3.76 (m, 1H), 3.48 (m, 1H), 1.66-1.96 (m, 2H), 1.48-1.64 (m, 2H), 1.21-1.44 (m, 2H), 1.38 (s, 9H).

Preparation 10 tert-Butyl N-(2-oxocyclopentyl)carbamate

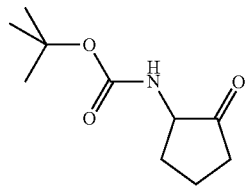

2,2,6,6-Tetramethylpiperidine-N-oxide (2.2 g, 14.2 mmol) and potassium bromide (8.5 g, 71 mmol) are added to a solution of racemic trans-tert-butyl N-[2-hydroxycyclopentyl]carbamate (75 g, 283 mmol) in dichloromethane (285 mL). The mixture is cooled to 5° C. with stirring. A freshly prepared ice cooled (5° C.) sodium hypochlorite aqueous solution (766 mL, 566 mmol, pH adjusted to 7.5-8 by addition of 10 g of solid potassium carbonate) is added with stirring to the reaction mixture while keeping the temperature below 5° C. The mixture is stirred at 5° C. for an additional 30 min. The reaction mixture is diluted with saturated aqueous sodium chloride solution (150 mL). The organic layer is separated and evaporated. The oily red residue is purified over a silica gel pad, eluting with EtOAc/hexanes (1/3) to obtain the title compound as a cream colored solid (43 g, 76%). $^1$H-NMR (300 MHz, DMSO-$d_6$) δ 6.99 (d, 1H, NH), 3.76 (q, 1H), 1.63-2.31 (m, 6H), 1.37 (s, 9H).

Preparation 11 tert-Butyl-2-[hydroxy-2-methyl-cyclopentyl]carbamate

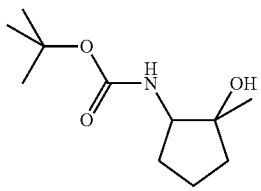

A solution of tert-butyl N-(2-oxocyclopentyl)carbamate (racemic) (25 g, 125.5 mmol) in diethyl ether (250 mL) is cooled to −5° C. Methylmagnesium bromide (125 mL, 375 mmol, 3 M in diethyl ether) is added, keeping the temperature at 0° C. The reaction is vigorously stirred and warmed to 22° C. over 2 h and then is allowed to warm to room temperature overnight. The reaction mixture is cooled to 5° C. and quenched by the addition of a cooled (5° C.) saturated solution of ammonium chloride (150 mL). The mixture is warmed to room temperature. The phases are separated and the aqueous phase is extracted with MTBE (3×150 mL). The combined organic portions are dried over sodium sulfate, filtered, and concentrated under reduced pressure to obtain the title compound (26.4 g, 78%) as crude material which is used without further purification.

Preparation 12

2-Amino-1-methyl-cyclopentanol, hydrochloride

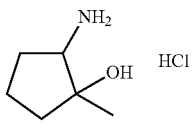

To a solution of tert-butyl-2-hydroxy-2-methyl-cyclopentylcarbamate (25 g, 104.5 mmol) in dichloromethane (210 mL) is added hydrogen chloride in dioxane (156 mL, 6 mol, 4 M) and the reaction is stirred at room temperature for 3 h. The solvent is evaporated and the resulting material is dried under vacuum to a constant weight to obtain the title compound (20.4 g) as a dark brown oil which is used in the next step without further purification. GC-MS 115.1 (M+); GC-MS analysis shows a cis/trans mixture in about a 3/2 ratio.

Second Alternate Preparation of 2-amino-1-methyl-cyclopentanol

Preparations 13-18

Preparation 13

[(1S,2S)-2-azidocyclopentoxy]-trimethyl-silane

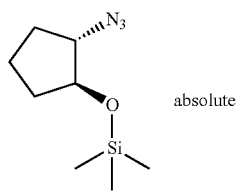

Cis-1,2-epoxycyclopentane (11.0 g, 131 mmol) is treated with (1R,2R)-(−)-1,2-cyclohexanediamino-N,N'-bis(3,5-di-t-butylsalicylidene)cobalt (II) (1.58 g, 2.62 mmol). The mixture is stirred for 5 min at room temperature, treated with azidotrimethylsilane (20.9 mL, 18.1 g, 157 mmol), and heated to 50° C. for 16 h. The reaction is diluted with EtOAc, hexanes, and diethyl ether, followed by addition of diatomaceous earth. The mixture is filtered through a pad of diatomaceous earth which is then rinsed with diethyl ether and hexanes. The filtrate is concentrated to give the crude product as a black oil. The crude material is purified on silica gel (660 g, 0-2% EtOAc/hexanes, observed on TLC with KMnO$_4$ staining) to give the title compound as a pale yellow oil 15.98 g (61%). $^1$H-NMR (400 MHz, CDCl$_3$) δ 4.00-3.96 (m, 1H), 3.65-3.61 (m, 1H), 2.05-1.99 (m, 1H), 1.93-1.89 (m, 1H), 1.80-1.75 (m, 2H), 1.58-1.53 (m, 2H), 0.13 (s, 9H).

Preparation 14 tert-Butyl N-[(1S,2S)-2-trimethylsilyloxycyclopentyl]carbamate

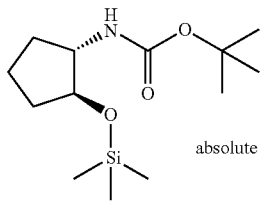 [SMILES: CC(C)(C)OC(=O)N[C@H]1CCC[C@@H]1O[Si](C)(C)C]

A solution of [(1S,2S)-2-azidocyclopentoxy]-trimethyl-silane (15.4 g, 77.6 mmol) in EtOH (141 mL) is treated with 10% palladium on carbon (1.82 g, 1.71 mmol) and hydrogenated (60 psi) overnight at room temperature. The reaction mixture is filtered through diatomaceous earth and rinsed with EtOH (50 mL). The filtrate is concentrated in vacuo and dissolved in acetone (81 mL). Water (81 mL) and sodium carbonate (8.17 g, 77.1 mmol) are added. The mixture is cooled to 0° C. and then treated with di-t-butyldicarbonate (18.6 g, 85.3 mmol). The reaction is stirred for 72 h at room temperature and then concentrated in vacuo to remove the acetone. The mixture is extracted with EtOAc (3×150 mL). The combined organic extracts are dried over sodium sulfate, filtered, and concentrated to give the title compound as a yellow oil (15.5 g, 73%). GC-MS m/z 156 (M-NHBoc)$^+$, 202 (M-Si(Me$_3$))$^+$.

Preparation 15 tert-Butyl N-[(1S,2S)-2-hydroxycyclopentyl]carbamate

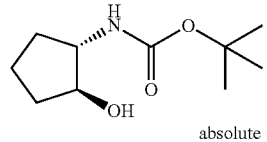

tert-Butyl N-[(1S,2S)-2-trimethylsilyloxycyclopentyl]carbamate (15.5 g, 56.7 mmol) and tetrabutylammonium fluoride (85.0 mL, 85.0 mmol) in THF (113 mL) are stirred at room temperature for 1 h. Water (50 mL) is added and the mixture is concentrated in vacuo to remove the THF. The resulting mixture is extracted with EtOAc (3×75 mL). The combined organic portions are washed with brine (2×30 mL), dried over sodium sulfate, filtered, and concentrated to give 14.7 g of crude product as a yellow oil. The material is purified on silica gel (330 g) using 25% EtOAc/hexanes to give the title compound as a white solid (10.25 g, 90%). LC-ES/MS m/z 224 (M+Na).

Preparation 16 tert-Butyl N-[(1S)-2-oxocyclopentyl]carbamate

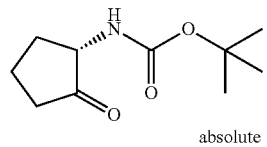

A mixture of oxalyl chloride (6.47 mL, 74.5 mmol) in THF (166 mL) is cooled to −72° C. under nitrogen and treated dropwise with DMSO (10.59 mL, 149.1 mmol). The mixture is stirred for 5 min, whereupon tert-butyl (1S,2S)-2-hydroxy-cyclopentylcarbamate (10.0 g, 49.7 mmol) is added. Stirring is continued at −75° C. for 45 min. Triethylamine (37.4 mL, 268.3 mmol) is added slowly keeping the temperature below −68° C. After the addition is complete the reaction is allowed to warm slowly to room temperature overnight. The reaction is combined with the reaction mixture from a pilot reaction (200 mg scale) completed earlier. Water (100 mL) is added and the reaction is concentrated in vacuo to remove THF. The mixture is extracted with EtOAc (3×150 mL). The combined organic portions are dried over sodium sulfate, filtered, and concentrated to give 12.41 g of crude product as a yellow oil. The material is purified on silica gel (330 g, 10-40% EtOAc/hexanes) to give the title compound (9.17 g, 93%). $^1$H-NMR (400 MHz, CDCl$_3$) δ 5.04-5.02 (m, 1H), 3.98-3.96 (m, 1H), 2.65-2.63 (m, 1H), 2.44-2.39 (m, 1H), 2.21-2.11 (m, 1H), 2.04 (s, 1H), 1.89-1.85 (m, 1H), 1.66-1.59 (m, 1H), 1.44 (s, 9H). GC-MS m/z 199 (M$^+$). [α]$_D^{20}$=+96.9° (c 1.0, CHCl$_3$) [literature (Aube, J.; Wolfe, M. S.; Yantiss, R. K.; Cook, S. M.;

Takusagawa, F. *Synthetic Communications* 1992, 22, 3003-3012) [a]$_D^{25}$=+125° (c 0.2, CHCl$_3$)].

Preparation 17 tert-Butyl N-[(1S)-2-hydroxy-2-methyl-cyclopentyl]carbamate

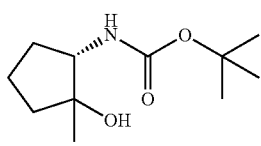

To a solution of tert-butyl N-[(1S)-2-oxocyclopentyl]carbamate (9.04 g, 45.4 mmol) in diethyl ether (227 mL) at 0° C. under nitrogen is added methylmagnesium bromide (37.8 mL, 113.4 mmol, 3.0 M in diethyl ether) dropwise. The reaction is warmed to room temperature and stirred for 2 h. An aliquot is worked up and analyzed by NMR to show that the reaction looks complete. The reaction was carefully quenched with saturated aqueous ammonium chloride (10 mL) and water (100 mL). EtOAc (200 mL) and 1 N HCl (50 mL) are added to dissolve a white precipitate. The layers are separated and the aqueous portion extracted with EtOAc (2×200 mL). The combined organic portions are dried over sodium sulfate, filtered, and concentrated to give a yellow oil (9.48 g). Analysis by GC-MS and NMR showed about 20% starting material still remaining. The material (7.25 g) is redissolved in diethyl ether (227 mL) and cooled to 0° C. Methylmagnesium bromide (13.2 mL, 39.5 mmol) is added portionwise, keeping the temperature below 7° C. The reaction is warmed to room temperature and another portion of methylmagnesium bromide (15.1 mL, 45.4 mmol) is added portionwise. The reaction is allowed to stir at room temperature overnight at which time GC-MS shows 5% starting material remaining. The reaction is quenched carefully with saturated aqueous ammonium chloride (20 mL). Water (200 mL) and 5 N HCl (20 mL) are added and the mixture extracted with EtOAc (3×300 mL). The combined organic portions are dried over sodium sulfate, filtered, and concentrated to give a dark amber oil (6.97 g). GC-MS m/z 158 (M-tBu)$^+$. GC-MS analysis shows a cis/trans mixture in a 68:32 ratio. Use as is without further purification.

Preparation 18

(2S)-2-amino-1-methyl-cyclopentanol hydrochloride

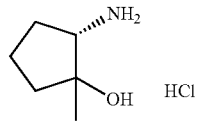

A solution of tert-butyl N-[(1S)-2-hydroxy-2-methyl-cyclopentyl]carbamate (mixture of cis and trans diastereomers) (6.66 g, 30.9 mmol), 4 M HCl in dioxane (46.4 mL, 185.6 mmol), and dichloromethane (62 mL) is stirred at room temperature for 1 h. The reaction is concentrated in vacuo, and then redissolved in MeOH and reconcentrated to give the title compound as a brown oil (5.09 g). LC-ES/MS m/z 116 (M+1).

Preparation 19

2-amino-1-methyl-cyclohexanol, hydrochloride

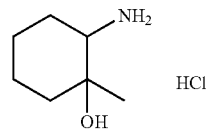

Methyl magnesium bromide (4.7 mL, 14.1 mmol, 3 M in diethyl ether) is added dropwise to a stirring solution of tert-butyl-2-oxo-cyclohexylcarbamate (1.00 g, 4.69 mmol) in diethyl ether (50 mL) at −78° C. After the addition is complete, the reaction is allowed to warm to room temperature and stirred for 22 h. The reaction is quenched with dilute hydrochloric acid and extracted two times with EtOAc. The organic portions are combined and dried over sodium sulfate, filtered, and concentrated in vacuo to yield the crude title compound (1.02 g) as a probable mixture of tert-butyl N-(2-hydroxy-2-methyl-cyclohexyl)carbamate, ES-MS m/z 252 (M+Na and the cyclized compound, 7a-methyl-3,3a,4,5,6,7-hexahydro-1,3-benzoxazol-2-one. ES-MS m/z 156 (M+1). The crude material was used as is without further purification.

The material is dissolved in 1,4-dioxane (15 mL) and treated with 12 M hydrochloric acid (1.1 mL) with stirring at room temperature for 3 days. The reaction is concentrated in vacuo, diluted with MeOH, and reconcentrated and dried in vacuo to yield the title compound (730 mg, 94% for 2 steps). ES-MS m/z 130.1 (M+1).

Preparation 20

3,6-Dihydro-2H-pyran

4-Bromotetrahydropyran (20 g, 121 mmol) and 5 N sodium hydroxide (30 mL) are stirred and heated at 90° C. for 18 h. The mixture is cooled to room temperature and the organic layer is separated from the aqueous. The organic layer, containing product only, is poured into a pre-weighed flask containing sodium sulfate for drying, which yields the title compound as a pale yellow oil (9.99 g, 98%). The title compound is stored over sodium sulfate as volatility prevents any filtering, rinsing, and concentration in vacuo. $^1$H NMR (400 MHz, DMSO-d$_6$) δ 5.78-5.74 (m, 1H), 5.69-5.66 (m, 1H), 3.96-3.94 (m, 2H), 3.61 (t, J=5.5 Hz, 2H), 2.01-1.99 (m, 2H).

Preparation 21

4,7-Dioxabicyclo[4.1.0]heptane

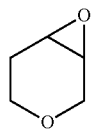

MCPBA (29.28 g, 130.6 mmol, 77 wt/wt %) is added to a solution of 3,6-dihydro-2H-pyran (9.99 g, 118.8 mmol) in dichloromethane (100 mL) at 0° C. and stirred for 1 h before allowing to warm to room temperature and stirring for 18 h. A saturated aqueous solution of sodium bicarbonate is carefully added and the mixture stirred vigorously. The organic layer is separated from the aqueous, dried over sodium sulfate, filtered, and concentrated in vacuo to yield the title compound (9.7 g, 82%). $^1$H NMR (400 MHz, DMSO-$d_6$) δ 3.84 (dd, J=2.7, 13.4 Hz, 1H), 3.74-3.70 (m, 1H), 3.38-3.26 (m, 3H), 3.10-3.09 (m, 1H), 1.87-1.82 (m, 2H).

Preparation 22 trans-4-Azidotetrahydropyran-3-ol

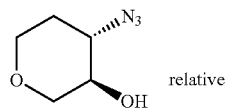

Sodium azide (50.4 g, 775 mmol) is added to a stirring solution of 4,7-dioxabicyclo[4.1.0]heptane (9.7 g, 96.9 mmol) and ammonium chloride (23.0 g, 426 mmol) in methanol (484 mL) and water (97 mL), and heated to 65° C. under nitrogen for 18 h. The mixture is cooled to room temperature and water (200 mL) is added. The methanol is removed in vacuo and the remaining aqueous layer is extracted with EtOAc (3×). The organic portions are combined, dried over sodium sulfate, filtered, and concentrated in vacuo to yield the title compound as a tan oil (5.63 g, 41%). $^1$H NMR (400 MHz, DMSO-$d_6$) δ 5.40-5.33 (m, 1H), 3.78-3.74 (m, 2H), 3.40-3.32 (m, 3H), 2.97-2.90 (m, 1H), 1.82-1.77 (m, 1H), 1.46-1.41 (m, 1H).

Preparation 23 trans-4-Aminotetrahydropyran-3-ol

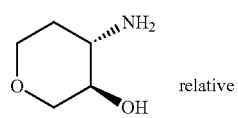

A mixture of trans-4-azidotetrahydropyran-3-ol (5.63 g, 39.3 mmol) and 10% Pd/C (2.09 g, 1.97 mmol) in methanol (157 mL) is hydrogenated (45 psi) at room temperature for 18 h. After filtering the mixture through diatomaceous earth, the filtrate is concentrated in vacuo to yield the title product as a tan semisolid (4.8 g, quantitative). ES-MS m/z 118.1 (M+1).

Preparation 24 trans-4-Azidotetrahydrofuran-3-ol

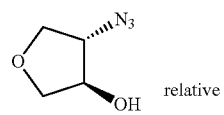

The title compound is prepared by essentially following the procedure as described for Preparation 22, using 3,4-epoxytetrahydrofuran. The crude product is obtained as a pale yellow oil (10.5 g). GC-MS m/z 129 (M$^+$).

Preparation 25 trans-tert-Butyl N-[4-hydroxytetrahydrofuran-3-yl]carbamate

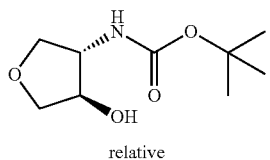

A solution of trans-4-azidotetrahydrofuran-3-ol (9.55 g, 74.0 mmol) in ethanol (247 mL) is treated with 10% palladium on carbon (787 mg, 0.370 mmol) and stirred for 16 h at room temperature under 60 psi of hydrogen. The reaction mixture is filtered through diatomaceous earth and rinsed with EtOH (100 mL). The filtrate is concentrated in vacuo and dissolved in acetone (77 mL). Water (77 mL) and sodium carbonate (7.79 g, 73.5 mmol) are added and the mixture is cooled to 0° C. before adding di-t-butyldicarbonate (17.8 g, 81.3 mmol). The reaction is stirred for 72 h at room temperature and then concentrated in vacuo. The mixture is extracted with EtOAc (3×300 mL), and the combined organic extracts dried over magnesium sulfate, filtered, and concentrated to give the title compound as a white solid (10.71 g, 71%). $^1$H NMR (400 MHz, CDCl$_3$) δ 4.82-4.81 (m, 1H), 4.28 (d, J=0.3 Hz, 1H), 4.10-4.02 (m, 2H), 3.96-3.95 (m, 1H), 3.69 (dd, J=3.0, 10.0 Hz, 1H), 3.61 (dd, J=3.0, 9.5 Hz, 1H), 3.29-3.27 (m, 1H), 1.48-1.44 (m, 9H).

Preparation 26 tert-Butyl N-(4-oxotetrahydrofuran-3-yl)carbamate

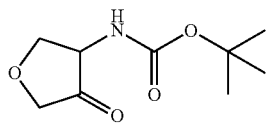

A mixture of oxalyl chloride (3.20 mL, 36.9 mmol) in THF (137 mL) is cooled to −78° C. under nitrogen and treated dropwise with DMSO (5.24 mL, 73.8 mmol). The mixture is stirred for 20 min at −78° C., whereupon trans-tert-butyl N-[4-hydroxytetrahydrofuran-3-yl]carbamate (5.00 g, 24.6 mmol) is added. Stirring at −78° C. is continued for 1 h. Triethylamine (18.5 mL, 133 mmol) is added and the reaction is warmed to room temperature. The reaction is stirred for 16 h, then water (100 mL) is added and the reaction is concentrated in vacuo to remove THF. The mixture is extracted with EtOAc (3×70 mL), the combined organics dried over magnesium sulfate, filtered, and concentrated to give 6.4 g of crude product as an orange oil. The crude product is purified on silica gel (220 g, 15-30% EtOAc/hexanes) to give the title compound as a yellow oil (2.20 g, 44%). GC-MS m/z 201 (M)⁺, 143 (M-t-Bu)⁺.

Preparation 27 and 28 cis-tert-Butyl N-[4-hydroxy-4-methyl-tetrahydrofuran-3-yl]carbamate and trans-tert-Butyl N-[4-hydroxy-4-methyl-tetrahydrofuran-3-yl]carbamate

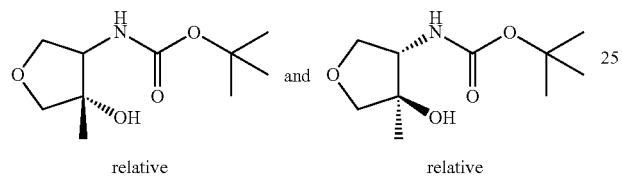

relative                        relative

To a solution of tert-butyl N-(4-oxotetrahydrofuran-3-yl)carbamate (2.12 g, 10.5 mmol) in diethyl ether (53 mL) at 0° C. under nitrogen is added methylmagnesium bromide (10.5 mL, 31.6 mmol, 3.0 M in diethyl ether) portionwise. The reaction is warmed to room temperature and stirred for 16 h. The reaction is carefully quenched with saturated aqueous ammonium chloride (10 mL) and water (100 mL). The reaction mixture is extracted with EtOAc (3×70 mL), the combined organic portions dried over MgSO₄, filtered, and concentrated to give crude product as a yellow oil (2.11 g). The material is purified on silica gel [80 g, 10-30% EtOAc/(1:1 dichloromethane/hexanes)]. The first-eluting diastereomer is racemic tert-butyl N-[(3S,4S)-4-hydroxy-4-methyl-tetrahydrofuran-3-yl]carbamate (and enantiomer) obtained as a colorless oil (1.04 g, 45%). Cis stereochemistry assigned on the basis of NMR of Example 10. LC-ES/MS m/z 240 (M+Na). The second-eluting product is racemic tert-butyl N-[(3S,4R)-4-hydroxy-4-methyl-tetrahydrofuran-3-yl]carbamate (and enantiomer) obtained as a white solid (460 mg, 20%). Trans stereochemistry based on NMR of Example 11. LC-ES/MS m/z 240 (M+Na).

Preparation 29 trans-4-Amino-3-methyl-tetrahydrofuran-3-ol hydrochloride

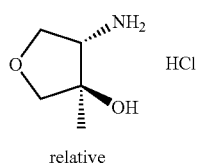

relative

A solution of racemic tert-butyl N-[(3S,4R)-4-hydroxy-4-methyl-tetrahydrofuran-3-yl]carbamate (450 mg, 2.07 mmol), 4.0 M HCl in dioxane (5.2 mL, 21 mmol), dioxane (5 mL), and methanol (0.8 mL) is stirred at room temperature for 16 h. The reaction mixture is concentrated in vacuo. The resulting residue is slurried in dichloromethane and concentrated in vacuo, followed by dissolution in MeOH and concentration in vacuo to give the crude title compound as a tan oil (366 mg, quantitative). LC-ES/MS m/z 118 (M+1).

Preparation 30 cis-4-Amino-3-methyl-tetrahydrofuran-3-ol hydrochloride

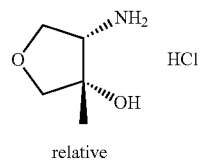

relative

The title compound is prepared by essentially following the procedure as described in Preparation 29, using cis tert-butyl N-[(3S,4S)-4-hydroxy-4-methyl-tetrahydrofuran-3-yl]carbamate (racemic). ¹H-NMR (400 MHz, DMSO-d₆) δ 8.18-8.17 (m, 2H), 3.99-3.94 (m, 1H), 3.68-3.64 (m, 2H), 3.54 (d, J=8.35 Hz, 1H), 3.41-3.39 (m, 1H), 1.31 (s, 3H).

Preparation 31

(3S,4R)-4-Trimethylsilyloxytetrahydrofuran-3-amine

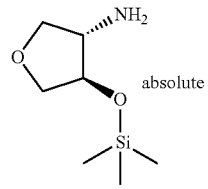

absolute

A mixture of [(3R,4S)-4-azidotetrahydrofuran-3-yl]oxy-trimethyl-silane (870 mg, 4.2 mmol; prepared according to the exact procedure found in Jacobsen, E. N.; Larrow, J. F.; Schaus, S. E. *J. Org. Chem.* 1997, 62, 4197-4199; except that commercially available (1R,2R)-(−)-1,2-cyclohexanediamino-N,N'-bis(3,5-di-t-butylsalicylidene)cobalt (II) is used as catalyst), 10% palladium on carbon (230 mg, 216 μmol), and THF (22 mL) is stirred at room temperature under hydrogen (60 psi) for 16 h. The reaction is filtered through a pad of diatomaceous earth and the pad is rinsed with THF (50 mL). The filtrate is concentrated in vacuo to give the title compound as a brown oil (825 mg, quantitative). LC-ES/MS m/z 176 (M+1).

Preparation 32

(3R,4S)-4-Trimethylsilyloxytetrahydrofuran-3-amine

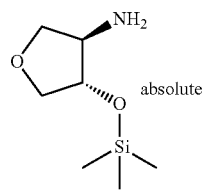

The title compound is prepared by essentially following the procedure described in Preparation 31 using [(3S,4R)-4-azidotetrahydrofuran-3-yl]oxy-trimethyl-silane (9.34 g, 46.4 mmol; prepared in opposing stereochemical configuration compared to the procedure found in Jacobsen, E. N.; Larrow, J. F.; Schaus, S. E. *J. Org. Chem.* 1997, 62, 4197-4199; except using commercially available (1S,2S)-(+)-1,2-cyclohexanediamino-N,N'-bis(3,5-di-t-butylsalicylidene)cobalt (II) as catalyst) to provide a colorless oil (7.55 g, 93%). LC-ES/MS m/z 176 (M+1).

Preparation 33

(3S,4S)-4-(tert-Butyl(dimethyl)silyl)oxytetrahydrofuran-3-ol

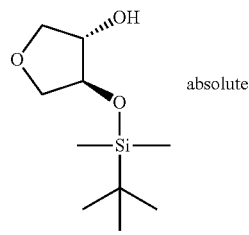

A mixture of (3S,4S)-tetrahydrofuran-3,4-diol (9.35 g, 89.8 mmol), t-butyldimethylchlorosilane (14.9 g, 98.8 mmol), TEA (13.8 mL, 98.8 mmol), and dichloromethane (100 mL) is stirred at room temperature for 4 days. The reaction is concentrated in vacuo and purified on silica gel (330 g, 35-80% EtOAc/hexanes, observed on TLC using KMnO$_4$ staining) to give 3.66 g (19%) of the title compound as a light yellow oil. GC-MS m/z 161 (M-tBu)$^+$.

Preparation 34 [(3S,4S)-4-(tert-Butyl(dimethyl)silyl)oxytetrahydrofuran-3-yl]methanesulfonate

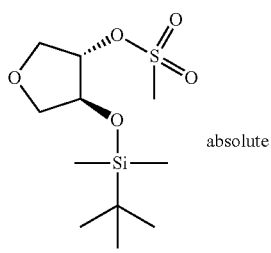 [SMILES: CC(C)(C)[Si](C)(C)O[C@H]1COC[C@@H]1OS(C)(=O)=O]

Under nitrogen, a solution of (3S,4S)-4-(tert-butyl(dimethyl)silyl)oxytetrahydrofuran-3-ol (3.30 g, 15.1 mmol), 2,6-lutidine (0.200 mL, 1.72 mmol), and diisopropylethylamine (2.90 mL, 16.6 mmol) in dichloromethane (50 mL) is cooled to –10° C. and treated slowly with methanesulfonyl chloride (1.23 mL, 15.9 mmol). The reaction is warmed up to room temperature and stirred for 16 h. A second addition of methanesulfonyl chloride (0.351 mL, 4.53 mmol) is added and the reaction is stirred at room temperature for a further 16 h. The reaction is shaken with dilute aqueous HCl and dichloromethane. The layers are separated and the organic portion is dried over Na$_2$SO$_4$, filtered, and concentrated in vacuo to give the title compound as a pale yellow oil (3.99 g, 89%). GC-MS m/z 239 (M-tBu)$^+$.

Preparation 35

[(3R,4R)-4-Azidotetrahydrofuran-3-yl]oxy-tert-butyl-dimethyl-silane

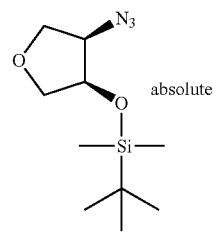

[(3S,4S)-4-(Tert-butyl(dimethyl)silyl)oxytetrahydrofuran-3-yl]methanesulfonate (3.00 g, 10.1 mmol) is dissolved in DMF (50 mL). Sodium azide (1.32 g, 20.2 mmol) is added and the reaction is heated to 60° C. for 72 h. Tetra-n-butylammonium iodide (0.400 g, 1.08 mmol) is added and the temperature is raised to 120° C. for 14 days. Water is added and the product is extracted into EtOAc. The organic layer is washed with water a second time and then dried over magnesium sulfate, filtered, and concentrated to give 2.9 g of crude product as a pale yellow oil. The crude product is purified on silica gel (120 g, 2-20% EtOAc/hexanes, observed on TLC with KMnO$_4$ staining) to give the title compound as a colorless oil (1.3 g, 53%). GC-MS m/z 186 (M-tBu)$^+$.

Preparation 36

(3R,4R)-4-(tert-Butyl(dimethyl)silyl)oxytetrahydrofuran-3-amine

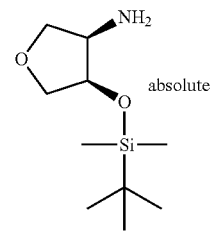

A mixture of [(3R,4R)-4-azidotetrahydrofuran-3-yl]oxy-tert-butyl-dimethyl-silane (1.27 g, 5.22 mmol) and 10% palladium on carbon (25 mg, 0.023 mmol) in ethanol (20 mL) is stirred at room temperature under a hydrogen balloon for 16 h. The reaction is filtered through a pad of diatomaceous earth and the filtrate is concentrated in vacuo to give the title compound as a colorless oil (1.0 g, 88%). LC-ES/MS m/z 218 (M+1).

Preparation 37

2-Methylcyclopent-2-en-1-ol

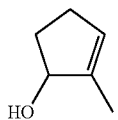

Sodium borohydride (8.86 g, 234 mmol) 15 awed to a solution of 2-methyl-2-cyclopenten-1-one (20.7 g, 215 mmol) in diethyl ether (430 mL) at −30° C. under nitrogen. The reaction is warmed up to 0° C. and treated with methanol (9.48 mL, 234 mmol). The reaction is warmed up to room temperature and stirred for 16 h. The reaction is treated with methanol (9.48 mL, 234 mmol), and then 1 h later treated again with methanol (9.48 mL, 234 mmol). The reaction is stirred for 72 h at room temperature, treated with brine (200 mL) and extracted into diethyl ether (3×300 mL). The combined organic portions are dried over magnesium sulfate, filtered, and concentrated in vacuo using a 30° C. water bath to afford the title compound as a colorless oil (24.2 g, quantitative). GC-MS m/z 98 (M+).

Preparation 38 tert-Butyl-(2-methylcyclopent-2-en-1-yl)oxy-diphenyl-silane

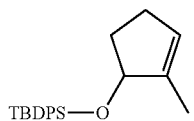

To a solution of 2-methylcyclopent-2-en-1-ol (23.06 g, 235.0 mmol), 1H-imidazole (32.0 g, 470 mmol) and N,N-dimethyl-4-pyridinamine (5.74 g, 47.0 mmol) in dichloromethane (470 mL) at room temperature is added tert-butylchlorodiphenylsilane (90.41 g, 328.94 mmol) over 15 min. After stirring the reaction mixture at room temperature for 16 h, water (300 mL) is added and the layers are separated. The aqueous layer is extracted with dichloromethane (2×200 mL). The combined organic portions are dried over sodium sulfate, filtered, and concentrated to give the crude product (108 g) as a colorless oil. The crude product is purified in 20 g batches on 330 g silica gel using 0-20% dichloromethane/hexane (product observed on TLC using KMnO4 staining) to give the title compound as a colorless oil (25.3 g, 32%). $^{1}$H-NMR (400 MHz, CDCl$_3$) δ 7.72-7.69 (m, 4H), 7.44-7.41 (m, 6H), 5.44- 5.41 (m, 1H), 4.72-4.70 (m, 1H), 2.33-2.29 (m, 1H), 2.06-2.01 (m, 2H), 1.74-1.69 (m, 1H), 1.66-1.65 (m, 3H), 1.09 (s, 9H).

Preparation 39 and Preparation 40 rel-tert-Butyl-[[(1S,4S,5S)-5-methyl-6-oxabicyclo[3.1.0]hexan-4-yl]oxy]-diphenyl-silane, Diastereomer 1 and rel-tert-Butyl-[[(1R,4S,5R)-5-methyl-6-oxabicyclo[3.1.0]hexan-4-yl]oxy]-diphenyl-silane, Diastereomer 2

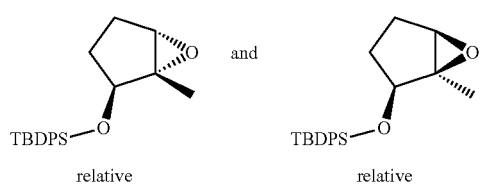

MCPBA (77% wt, 5.03 g, 22.5 mmol, 0.8 eq) is added to a 0° C. solution of tert-butyl-(2-methylcyclopent-2-en-1-yl)oxy-diphenyl-silane (9.45 g, 28.1 mmol) in dichloromethane (94 mL) and saturated aqueous sodium bicarbonate (28 mL). The reaction is stirred for 16 h at room temperature and then treated with more MCPBA (77% wt, 2.52 g, 11.2 mmol, 0.4 equiv) and saturated aqueous sodium bicarbonate (56 mL). After stirring for 2 h at room temperature the reaction is quenched by adding saturated aqueous Na$_2$SO$_3$ solution and stirring for 30 min at room temperature. The reaction is extracted with dichloromethane (3×70 mL). The combined organic portions are dried over sodium sulfate, filtered, and concentrated. The crude product is purified on silica gel (330 g, 30-60% dichloromethane/hexanes). The first eluting product from the silica gel column is rel-tert-butyl-[[(1S,4S,5S)-5-methyl-6-oxabicyclo[3.1.0]hexan-4-yl]oxy]-diphenyl-silane (mixture of enantiomers, relative stereochemistry determined by NMR analysis) (3.03 g, 31%, colorless oil). $^{1}$H-NMR (400 MHz, CDCl$_3$) δ 7.68-7.64 (m, 4H), 7.45-7.42 (m, 6H), 4.21-4.20 (m, 1H), 3.35 (s, 1H), 1.93-1.88 (m, 2H), 1.45 (s, 3H), 1.43-1.40 (m, 2H), 1.08 (s, 9H). LC-ES/MS m/z 353 (M+1). The second-eluting product from the silica gel column is rel-tert-butyl-[[(1R,4S,5R)-5-methyl-6-oxabicyclo[3.1.0]hexan-4-yl]oxy]-diphenyl-silane (mixture of enantiomers) (5.82 g, 59%, milky white oil). $^{1}$H-NMR (400 MHz, CDCl$_3$) δ 7.73-7.69 (m, 4H), 7.46-7.42 (m, 6H), 4.03 (t, J=7.9 Hz, 1H), 3.11 (s, 1H), 1.90-1.85 (m, 1H), 1.48-1.43 (m, 3H), 1.30 (s, 3H), 1.08 (s, 9H). LC-ES/MS m/z 353 (M+1).

Preparation 41 rel-(1S,2R,5S)-2-Azido-5-(tert-butyl(diphenyl)silyl)oxy-1-methyl-cyclopentanol

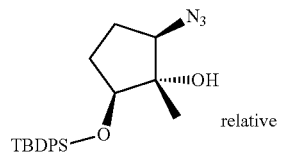

A mixture of rel-tert-butyl-[[(1S,4S,5S)-5-methyl-6-oxabicyclo[3.1.0]hexan-4-yl]oxy]-diphenyl-silane (enantiomeric mixture) (1.0 g, 2.8 mmoles), sodium azide (782 mg, 11.9 mmol), and DMF (10 mL) is stirred at 60° C. for 16 h. Lithium perchlorate (604 mg, 5.7 mmol) and additional sodium azide (931 mg, 14.2 mmol) are added and the reaction is heated to 90° C. for 72 h, then cooled to room temperature. The reaction is treated with water (50 mL) and extracted with EtOAc (3×70 mL). The combined organic portions are dried over magnesium sulfate, filtered, and concentrated to afford the title compound as a pale yellow oil (2.51 g). The material is carried forward crude without further purification or characterization.

Preparation 42 rel-(1S,2R,5R)-2-Azido-5-(tert-butyl(diphenyl)silyl)oxy-1-methyl-cyclopentanol

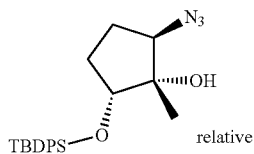

The title compound is prepared by essentially following the procedure as described in Preparation 41 using rel-tert-butyl-[[(1R,4S,5R)-5-methyl-6-oxabicyclo[3.1.0]hexan-4-yl]oxy]-diphenyl-silane (enantiomeric mixture), except that the reaction is heated to 90° C. for 48 h and the addition of lithium perchlorate and the second addition of sodium azide are omitted.

Preparation 43 rel-(1S,2R,5S)-2-Amino-5-(tert-butyl(diphenyl)silyl)oxy-1-methyl-cyclopentanol

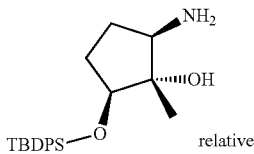

A mixture of rel-(1S,2R,5S)-2-azido-5-(tert-butyl(diphenyl)silyl)oxy-1-methyl-cyclopentanol (2.28 g, 5.76 mmol, enantiomeric mixture) and 10% palladium on carbon (61 mg) in ethanol (29 mL) is hydrogenated (60 psi) at room temperature for 16 h. The reaction is filtered through a pad of diatomaceous earth and rinsed with EtOH (50 mL). The filtrate is concentrated in vacuo, dissolved in dichloromethane (10 mL), and concentrated in vacuo. The crude product is purified on silica gel (120 g, 1-6% (2 M ammonia in methanol/dichloromethane) to afford the title compound as an opaque yellow oil (419 mg, 20%). LC-ES/MS m/z 353 (M+1).

Preparation 44 rel-(1S,2R,5R)-2-Amino-5-(tert-butyl(diphenyl)silyl)oxy-1-methyl-cyclopentanol

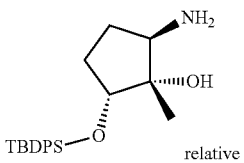

The title compound is prepared by essentially following the procedure describe in Preparation 43, using rel-(1S,2R,5R)-2-azido-5-(tert-butyl(diphenyl)silyl)oxy-1-methyl-cyclopentanol to provide the product as a pale yellow oil. LC-ES/MS m/z 370 (M+1).

Example 1

2-Chloro-4-[[(1R,2R)-2-hydroxy-2-methyl-cyclopentyl]amino]-3-methyl-benzonitrile

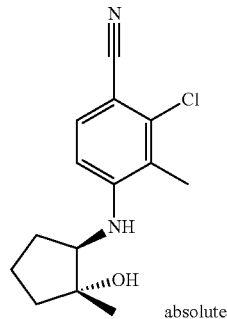 [SMILES: Cc1c(N[C@@H]2CCC[C@@]2(C)O)ccc(C#N)c1Cl]

In a glass pressure vessel, a mixture of trans-2-amino-1-methyl-cyclopentanol (8.75 g, 53 mmol, 1.5 eq), 2-chloro-4-fluoro-3-methyl-benzonitrile (6 g, 35.4 mmol) and lithium carbonate (7.84 g, 106 mmol) in DMSO (72 mL) and water (7.2 mL) is degassed for 15 min by bubbling nitrogen through the mixture. The vessel is sealed and heated at 130° C. for 36 h. After cooling to room temperature, the mixture is quenched over ice/water (700 mL) at 5° C. (internal temperature) with stirring. After 15 min, the initially sticky solid turns into a cream solid that is collected by filtration and washed with cold water. The solid is stirred over EtOAc (100 mL) for 30 min and filtered through a pad of diatomaceous earth. The EtOAc filtrate is concentrated to afford 15 g of a yellow solid. The material is purified by silica gel chromatography using dichloromethane to elute impurities and 10% EtOAc/dichloromethane to elute final product to obtain the racemic title compound (9.2 g, 98%). $^1$H NMR (400 MHz, DMSO-$d_6$) δ 7.48 (d, 1H), 6.90 (d, 1H), 5.51 (d, 1H), 4.66 (s, 1H), 3.65-3.74 (m, 1H), 2.21 (s, 3H), 2.01-2.13 (m, 1H), 1.50-1.78 (m, 5H), 1.07 (s, 3H). LC-ES/MS m/z ($^{35}$Cl/$^{37}$Cl) 265.2/267.1 (M+1). The compound is dissolved in MeOH (70 mL). The enantiomers are separated in 21 mg injections by supercritical fluid chromatography on two CHIRALPAK® AD-H columns (2×25 cm, 5 μm) stringed in series. Mobile phase: 20% isopropanol/carbon dioxide. Flow rate: 65 mL/min. Detection: 215 nm. Each run is 6.48 min. The first eluting peak is obtained as Isomer 1 and the second eluting peak is obtained as the title compound, Isomer 2 (4.13 g, 100% enantiomeric excess). The enantiomeric excess is determined by SFC on a CHIRALPAK® AD-H (4.6×100 mm, 5 μm) column using 20% isopropanol/carbon dioxide. Flow rate: 2.5 mL/min. Detection: 215 nm. Isomer 1 $T_R$=2.53 min. Isomer 2 (title compound) $T_R$=3.06 min.

Example 1A

Alternate Procedure

2-Chloro-4-[[(1R,2R)-2-hydroxy-2-methyl-cyclopentyl]amino]-3-methyl-benzonitrile

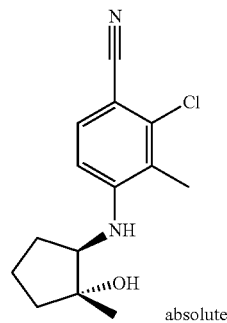 [SMILES: Cc1c(N[C@@H]2CCC[C@@]2(C)O)ccc(C#N)c1Cl]

absolute

The reaction below is carried out in six batches in parallel.

A mixture of trans-2-amino-1-methyl-cyclopentanol (34.93 g, 212.3 mmol), 2-chloro-4-fluoro-3-methyl-benzonitrile (30 g, 176.9 mmol), lithium carbonate (26.14 g, 353.8 mmol), DMSO (270 mL), water (30 mL) in a 420 mL pressure reactor is degassed for 15 min by bubbling nitrogen, sealed, and heated with vigorous stirring at 130° C. for 48 h. After cooling to room temperature, three of the batches are poured over water (9 L) and MTBE (1 L), stirred for 30 min, filtered through diatomaceous earth and transferred to a separation funnel. The organic layer is separated and the aqueous phase is washed twice with MTBE (2×1 L). The organic layers are combined, dried over sodium sulfate, filtered and concentrated in vacuo. The workup is repeated for the remaining three batches and all the lots are combined to isolate the desired crude product (400 g). The material is purified on silica gel, eluting with 0 to 10% EtOAc/dichloromethane to obtain pure racemic title compound (trans diastereomer) (280 g, 99%). The compound is dissolved at a concentration of 10.3 mg/mL in 25% isopropanol/75% heptanes mobile phase. The enantiomers are separated in portions of 1.16 g (113 mL) per injection by preparative HPLC on a CHIRALPAK® AD-H column (11×35 cm, 20 μm) using a steady state recycle (SSR) method (10.2 g/h throughput). Mobile phase: 25% isopropanol/heptane. Flow rate: 850 mL/min. Detection: 290 nm. The first eluting peak is obtained as Isomer 1 (>98% enantiomeric excess) and the second eluting peak is obtained as the title compound, Isomer 2 (137 g, 97.7% enantiomeric excess). The enantiomeric excess is determined by HPLC on a CHIRALPAK® AD-H (4.6×150 mm, 5 μm) column using 25% isopropanol/heptane. Flow rate: 0.6 mL/min. Detection: 270 nm. Isomer 1 $T_R$=6.7 min. The desired isomer is the $2^{nd}$ eluting under these chiral HPLC conditions. Isomer 2 (title compound) $T_R$=7.9 min.

Example 1B

Recrystillization and Single Crystal X-Ray for Determination of Absolute Stereochemistry
2-Chloro-4-[[(1R,2R)-2-hydroxy-2-methyl-cyclopentyl]amino]-3-methyl-benzonitrile

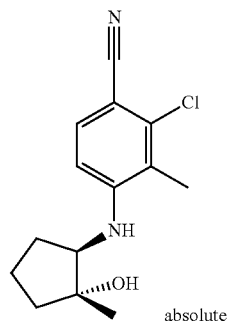 [SMILES: Cc1c(N[C@@H]2CCC[C@@]2(C)O)ccc(C#N)c1Cl]

absolute

2-Chloro-4-[[(1R,2R)-2-hydroxy-2-methyl-cyclopentyl] amino]-3-methyl-benzonitrile (21.62 g, 81.66 mmol) is placed in a round bottom flask provided with a heating mantel, an internal thermometer, and a stir bar. Acetone (33 mL) is added and the slurry is stirred and heated to 50° C. At this temperature, the yellowish solid goes into solution completely. The solution is heated to 60° C. Heptane is added slowly using an addition funnel. After adding 75 mL, every drop of solvent creates a cloudiness that disappears almost instantly upon stirring at 60° C. After additional heptanes (50 mL) the cloudiness takes longer to disappear since the solution is getting saturated. The solution stays cloudy and the addition of heptane is stopped. The temperature is raised to 62° C. and acetone (5 mL) is added which makes the solution completely clear again. Heptane (100 mL) is added dropwise making the solution cloudy again. The temperature is raised to 67° C. and acetone is distilled and collected in a Dean-Stark apparatus. The slurry is allowed to cool to room temperature gradually and left to sit for 18 h. The resulting white solid is filtered and placed on high vacuum. After 4 h on high vacuum a significant amount of acetone is observed to be present by NMR. Additional time on high vacuum did not remove the acetone. The material is slurried in hexane for 30 min, filtered, and placed on high vacuum again to give the final compound as a white solid (18.1 g). LC-ES/MS m/z 265.0 (M+1).

Determination of Absolute Stereochemistry:

The compound has a pronounced tendency to form solvated structures with nearly every solvent in which it has significant solubility. As proof of the molecule's absolute stereochemistry, crystals were formed using a chiral solvent such that the known chirality of its stereocenter could be related to the chirality of the unknown stereocenter of the drug molecule. This served as one source of determination of the absolute stereochemistry. A second method used for its determination was accomplished by refinement of the absolute structure parameter. The anomalous dispersion, in large part due to the "heavier" chlorine atom was sufficiently significant to conclude the absolute stereochemistry of the compound directly, as the parameter refined to a value of 0.054 (11). Both methods are commonly accepted methods for determination of chirality of unknown stereocenters of organic molecules by X-ray crystallography and afforded consistent results. The structure studied crystallized as a "hemi" solvate of S-(−)-methyl lactate as described herein, having a ratio of two drug molecules for one solvent molecule. 2-Chloro-4-[[(1R,2R)-2-hydroxy-2-methyl-cyclopentyl]amino]-3-methyl-benzonitrile (35 mg, taken from the 18.1 g lot described above) is dissolved in S-(−)-methyl lactate (500 µL). The sample vial is placed "lid-less" into a larger container, a 100 mL Pyrex® bottle that contains n-pentane, and the larger bottle is capped. Vapor diffusion is allowed to occur overnight, whereby the more volatile n-pentane diffused into the solution of 2-chloro-4-[[(1R,2R)-2-hydroxy-2-methyl-cyclopentyl]amino]-3-methyl-benzonitrile and S-(−) methyl lactate, effecting the growth of single crystals. The crystals were harvested by decanting off the excess solution. One of the large crystals was isolated and analyzed by single crystal X-ray diffraction. The data collection and results from the single crystal structure determination of this solvated form had the following characteristics.

A single crystal is mounted on a thin glass fiber at 100(2)° K. Data are collected using a CuK$_\alpha$ radiation source ($\lambda$=1.54178 Å) and a Bruker D8 based 3-circle goniometer diffractometer equipped with a SMART 6000CCD area detector (Bruker-AXS. Madison, Wis., USA). Cell refinement and data reduction are performed using the SAINT program V7.68a (Sheldrick, G. M. *SHELXS*86. *Acta Cryst.* (1990) A46, 467-473). The unit cell is indexed, having monoclinic parameters of a=7.5457(2) Å, b=17.1858(6) Å, c=12.3017(4) Å and $\beta$=97.6870(10)°. The cell volume of crystal structure was 1580.93(9) Å$^3$. The calculated density of the molecule is 1.331 g/cm$^3$ at 100° K. The structure is solved by direct methods (Sheldrick, G. M. *SHELXS*86. *Acta Cryst.* (1990) A46, 467-473). All non-hydrogen atomic parameters were independently refined. The space group choice of P2(1) was confirmed by successful convergence of the full-matrix least-squares refinement on F$^2$ (Sheldrick, G. M. (1993). *SHELXS*93). Program for crystal structure refinement. Institute fur anorg chemie, Göttingen, Germany) with a final goodness of fit of 1.038. The final residual factor, R$_1$, is 0.0344 and wR2 is 0.089. The largest difference peak and hole after the final refinement cycle are 0.239 and −0.298 (e·Å$^{-3}$), respectively. The absolute stereochemistry is determined by refinement of the absolute structure parameter to 0.054(11), indicating the stereochemistry of the molecule is as depicted (1R,2R).

X-ray Powder Diffraction Data (XRPD) Characterization of Anhydrous Forms

The XRD patterns of the crystals are obtained on a Bruker D4 Endeavor X-ray powder diffractometer, equipped with a CuK$\alpha$ source $\lambda$=1.54056 Å) and a Vantec detector, operating at 35 kV and 50 mA and with 1 mm divergence and receiving slits and a 0.1 mm detector slit. Each sample is scanned between 4 and 40° in 2θ. The dry powder is packed into recessed top-loading sample holder and a smooth surface is obtained using a glass slide. The crystal form diffraction patterns are collected at ambient temperature and relative humidity.

It is well known in the crystallography art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g., The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature or humidity at which a sample is analyzed, sample displacement, or the presence or absence of an internal standard. In the present case, a peak position variability of ±0.1 in 2θ will take into account these potential variations without hindering the unequivocal identification of the indicated crystal form.

Example 1C

2-Chloro-4-[[(1R,2R)-2-hydroxy-2-methyl-cyclopentyl]amino]-3-methyl-benzonitrile crystalline Form 1

2-Chloro-4-[[(1R,2R)-2-hydroxy-2-methyl-cyclopentyl]amino]-3-methyl-benzonitrile (430 mg) is dissolved into acetone (1 mL) to which heptane (5 mL) is added. The mixture is stirred at 60° C. The mixture is then allowed to concentrate to give a thick white slurry and heptane (3 mL) is incorporated as the concentration at 60° C. continues. The material is vacuum filtered to give 308 mg (72%) and further dried under vacuum at 70° C. overnight.

Confirmation of a crystal form may be made based on any unique combination of distinguishing peaks (in units of ° 2θ), typically the more prominent peaks. Thus, a prepared sample of 2-chloro-4-[[(1R,2R)-2-hydroxy-2-methyl-cyclopentyl]amino]-3-methyl-benzonitrile crystalline Form 1 is characterized by an XRD pattern using CuK$\alpha$ radiation as having diffraction peaks (2-theta values) as described in Table 1 below, and in particular having peaks at 9.18 in combination with one or more of the peaks selected from the group consisting of 14.87, 17.97, and 18.46; with a tolerance for the diffraction angles of 0.1 degrees.

TABLE 1

| X-ray powder diffraction peaks of Example 1C | | |
|---|---|---|
| Peak | Angle (2-theta °) | Intensity (%) |
| 1 | 9.18 | 100 |
| 2 | 14.87 | 44 |
| 3 | 15.12 | 15 |
| 4 | 17.97 | 26 |
| 5 | 18.46 | 16 |
| 6 | 21.84 | 9 |
| 7 | 22.77 | 7 |
| 8 | 23.07 | 8 |
| 9 | 23.87 | 9 |
| 10 | 24.40 | 8 |

Example 1D

2-Chloro-4-[[(1R,2R)-2-hydroxy-2-methyl-cyclopentyl]amino]-3-methyl-benzonitrile crystalline Form 2

The material recrystallized in Example 1B is used to characterize Form 2.

Confirmation of a crystal form may be made based on any unique combination of distinguishing peaks (in units of ° 2θ), typically the more prominent peaks. Thus, a prepared sample of 2-chloro-4-[[(1R,2R)-2-hydroxy-2-methyl-cyclopentyl]amino]-3-methyl-benzonitrile crystalline form 2 is characterized by an XRD pattern using CuK$\alpha$ radiation as having diffraction peaks (2-theta values) as described in Table 2 below, and in particular having peaks at 20.45 in combination with one or more of the peaks selected from the group consisting of 17.77, 16.15, and 12.59; with a tolerance for the diffraction angles of 0.1 degrees.

TABLE 2

X-ray powder diffraction peaks of Example 1D

| Peak | Angle (2-theta °) | Intensity (%) |
|---|---|---|
| 1 | 14.52 | 17 |
| 2 | 16.15 | 49 |
| 3 | 17.77 | 72 |
| 4 | 20.45 | 100 |
| 5 | 21.77 | 23 |
| 6 | 25.19 | 33 |
| 7 | 26.19 | 29 |
| 8 | 26.93 | 13 |
| 9 | 30.07 | 22 |
| 10 | 30.96 | 29 |
| 11 | 32.65 | 11 |
| 12 | 35.91 | 32 |
| 13 | 37.36 | 14 |

Example 1E

2-Chloro-4-[[(1R,2R)-2-hydroxy-2-methyl-cyclopentyl]amino]-3-methyl-benzonitrile crystalline ethanol solvate 2-Chloro-4-[[(1R,2R)-2-hydroxy-2-methyl-cyclopentyl]amino]-3-methyl-benzonitrile (104 mg) is weighed into a small sample vial. Ethanol (0.50 mL) is added. The sample is allowed to stir over the weekend. The material isolated is then characterized by X-ray diffraction. The pattern is collected quickly to minimize phase conversion, using the same settings as before, albeit with a larger step size of 0.017 degrees two-theta and 0.1 seconds per step.

Confirmation of a crystal form may be made based on any unique combination of distinguishing peaks (in units of ° 2θ), typically the more prominent peaks. Thus, a prepared sample of 2-chloro-4-[[(1R,2R)-2-hydroxy-2-methyl-cyclopentyl]amino]-3-methyl-benzonitrile crystalline ethanol solvate crystal form is characterized by an XRD pattern using CuKα radiation as having diffraction peaks (2-theta values) as described in Table 3 below, and in particular having peaks at 7.00 in combination with one or more of the peaks selected from the group consisting of 17.26, 23.34, and 12.30; with a tolerance for the diffraction angles of 0.2 degrees.

TABLE 3

X-ray powder diffraction peaks of Example 1E

| Peak | Angle (2-theta °) | Intensity (%) |
|---|---|---|
| 1 | 7.00 | 100 |
| 2 | 8.59 | 3 |
| 3 | 10.13 | 3 |
| 4 | 11.89 | 3 |
| 5 | 12.30 | 6 |
| 6 | 12.91 | 4 |
| 7 | 13.95 | 4 |
| 8 | 16.76 | 3 |
| 9 | 17.26 | 19 |
| 10 | 23.34 | 31 |

Example 1F

2-Chloro-4-[[(1R,2R)-2-hydroxy-2-methyl-cyclopentyl]amino]-3-methyl-benzonitrile crystalline isopropanol solvate 2-Chloro-4-[[(1R,2R)-2-hydroxy-2-methyl-cyclopentyl]amino]-3-methyl-benzonitrile (114 mg) is weighed into a small sample vial. Isopropanol (0.50 mL) is added. The sample is allowed to stir over the weekend. The material isolated is then characterized by X-ray diffraction.

Confirmation of a crystal form may be made based on any unique combination of distinguishing peaks (in units of ° 2θ), typically the more prominent peaks. Thus, a prepared sample of 2-chloro-4-[[(1R,2R)-2-hydroxy-2-methyl-cyclopentyl]amino]-3-methyl-benzonitrile crystalline isopropanol solvate crystal form is characterized by an X-ray powder diffraction pattern using CuKα radiation as having diffraction peaks (2-theta values) as described in Table 4 below, and in particular having peaks at 7.07 in combination with one or more of the peaks selected from the group consisting of 6.93, 17.12, and 23.13; with a tolerance for the diffraction angles of 0.2 degrees.

TABLE 4

X-ray powder diffraction peaks of Example 1F

| Peak | Angle (2-theta °) | Intensity (%) |
|---|---|---|
| 1 | 6.9 | 43 |
| 2 | 7.1 | 100 |
| 3 | 12.2 | 6 |
| 4 | 13.4 | 3 |
| 5 | 16.6 | 3 |
| 6 | 17.1 | 30 |
| 7 | 23.1 | 46 |
| 8 | 23.9 | 2 |
| 9 | 26.0 | 2 |
| 10 | 31.8 | 2 |

Example 1G

Large Scale Recrystillization

2-Chloro-4-[[(1R,2R)-2-hydroxy-2-methyl-cyclopentyl]amino]-3-methyl-benzonitrile In a 3 L 3-necked round bottom flask, 2-chloro-4-[[(1R,2R)-2-hydroxy-2-methyl-cyclopentyl]amino]-3-methyl-benzonitrile (131.4 g, 496.3 mmol) in acetone (200 mL) is heated to 50° C. until all the solids dissolve. The temperature is increased to 60° C. and heptane (approximately 1.35 L) is added slowly using an addition funnel. The temperature is raised to 65° C. and acetone (approximately 15 mL) is distilled and collected with a Dean-Stark trap. After 1 h the temperature is raised to 67° C. The solution is seeded with crystalline 2-chloro-4-[[(1R,2R)-2-hydroxy-2-methyl-cyclopentyl]amino]-3-methyl-benzonitrile (1 g) and acetone (approximately 80 mL) is distilled. Seed crystals can be obtained from Example 1B, or generated from the solids obtained in Example 1 or 1A, or can be obtained using other methods common to one skilled in the art, such as recrystallization of a small aliquot. After 1 h the heat is turned off and the slurry is left to cool down to room temperature slowly. The white solids are collected by filtration and left under vacuum overnight to obtain 116.0 g of product. Additional product (5.6 g) was collected by filtration from the mother liquor. In a 3 L flask, a slurry of the 116.0 g of product in hexanes (1.5 L) is seeded with 2-chloro-4-[[(1R,2R)-2-hydroxy-2-methyl-cyclopentyl]amino]-3-methyl-benzonitrile (approximately 2 g) and stirred for 4 h. The white solid is collected by filtration and is left under a nitrogen stream over 48 hours. Additional product (2.6 g) precipitates from the mother liquor and is collected by filtration. A total amount of 109.7 g of 2-chloro-4-[[(1R,2R)-2-hydroxy-2-methyl-cyclopentyl]amino]-3-methyl-benzonitrile is isolated. $^1$H NMR (400 MHz, DMSO-$d_6$) δ 7.47 (d, 1H), 6.90 (d, 1H), 5.48 (d, 1H), 4.64 (s, 1H), 3.65-3.74 (m, 1H), 2.19 (s, 3H), 2.01-2.13 (m, 1H), 1.50-1.78 (m, 5H), 1.03 (s, 3H). LC-ES/MS m/z ($^{35}$Cl/$^{37}$Cl) 265.2/267.2 (M+1). $[a]_D^{20}$=+20.2° (c 1.0, EtOH).

Example 2

2-Chloro-4-[[(1S,2R)-2-hydroxy-2-methyl-cyclopentyl]amino]-3-methyl-benzonitrile

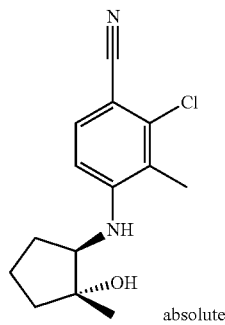 [SMILES: Cc1c(N[C@@H]2CCC[C@@]2(C)O)ccc(C#N)c1Cl]

absolute

In a sealed pressure vessel, a mixture of 2-chloro-4-fluoro-3-methyl-benzonitrile (1.2 g, 7.08 mmol), (1R,2S)-2-amino-1-methyl-cyclopentanol (1.63 g, 14.2 mmol) and lithium carbonate (1.10 g, 14.9 mmol) in DMSO (14.4 mL) and water (1.4 mL) is heated at 130° C. overnight. After allowing the reaction to cool to room temperature, the mixture is diluted with EtOAc and washed twice with 1 N hydrochloric acid. The organic phase is concentrated under reduced pressure and purified using radial chromatography eluting with EtOAc/hexanes (20 to 50% EtOAc/hexanes gradient). The resulting residue is repurified using radial chromatography with 1% methanol/dichloromethane. The isolated product is recrystallized with ether/hexanes, collected by filtration, and dried under reduced pressure to yield the title compound as a white solid (450 mg, 24%). A second crop (84 mg) is also isolated. LC-ES/MS m/z ($^{35}$Cl/$^{37}$Cl) 265/267 (M+1). $^1$H NMR (400 MHz, DMSO-$d_6$) δ 1.16 (s, 3H), 1.71-1.73 (m, 5H), 2.12-2.13 (m, 1H), 2.14 (s, 3H), 3.46-3.50 (m, 1H), 4.93 (s, 1H), 5.26-5.30 (m, 1H), 6.63 (d, J=8.8 Hz, 1H), 7.47 (d, J=8.6 Hz, 1H). Chiral HPLC showed the material had an enantiomeric excess of 67%. The enantiomeric excess is determined by SFC on a CHIRALPAK® AS-H (4.6×150 mm, 5 μm) column using 20% ethanol/carbon dioxide. Flow rate: 5 mL/min. Detection: 225 nm. Isomer 1 (title compound): $T_R$=1.39 min; Isomer 2: $T_R$=1.99 min. The absolute stereochemistry of Isomer 1 (1S,2R) is known by correlation of retentions times with Isomer 1 and Isomer 2 as described in Example 3.

The enantioenriched material (534 mg) is dissolved in methanol (5.5 mL) and purified in 500 μL injections by SFC on a CHIRALPAK® AS-H (2.1×25 cm, 5 μm) column using 20% ethanol/carbon dioxide. Flow rate: 70 mL/min. Detection: 225 nm. The title compound is isolated as the first eluting peak, Isomer 1 (326 mg) in 99% enantiomeric excess. The enantiomeric excess is determined by SFC as described above.

Alternate Procedure

Example 2A & 2B

Example 2A cis-2-Chloro-4-[[2-hydroxy-2-methyl-cyclopentyl]amino]-3-methyl-benzonitrile

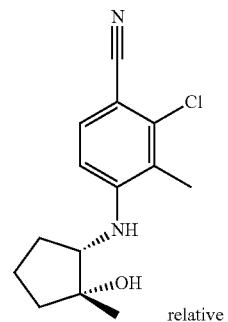 [SMILES: Cc1c(N[C@H]2CCC[C@@]2(C)O)ccc(C#N)c1Cl]

relative

2-Chloro-4-fluoro-3-methyl-benzonitrile (12.4 g, 73.2 mmol) is added to a solution of freshly prepared racemic 2-amino-1-methyl-cyclopentanol, hydrochloride (20.4 g) in DMSO (145 mL) in a pressure reactor vessel. Lithium carbonate (15.5 g, 209 mmol) and water (14.5 mL) are added. The mixture is stirred and degassed with nitrogen for 10 min. The reactor is sealed and the reaction stirred at 130° C. for 28 h. The mixture is cooled to room temperature and diluted with water (1 L) and MTBE (150 mL). The mixture is stirred for 10 min at room temperature and filtered through a pad of diatomaceous earth. The organic layer is separated and the aqueous layer extracted with MTBE (2×100 mL). The organic portions are combined, dried over sodium sulfate, filtered, and evaporated to afford crude material. The material is purified using silica gel chromatography eluting first with 100% methylene chloride to obtain the cis-2-chloro-4-[[2-hydroxy-2-methyl-cyclopentyl]amino]-3-methyl-benzonitrile compound (5.6 g, 20%). $^1$H NMR (300 MHz, DMSO-$d_6$) δ 7.47 (d, J=8.6 Hz, 1H), 6.63 (d, J=8.8 Hz, 1H), 5.26-5.30 (m, 1H), 4.93 (s, 1H), 3.46-3.50 (m, 1H), 2.14 (s, 3H), 2.12-2.13 (m, 1H), 1.71-1.73 (m, 5H), 1.16 (s, 3H). LC-ES/MS m/z 265.2 (M+1).

After isolation of the cis isomer, elution is continued using a mixture of methylene chloride/EtOAc (9/1) to afford (3.6 g, 12%) of the trans-2-chloro-4-[[2-hydroxy-2-methyl-cyclopentyl]amino]-3-methyl-benzonitrile. $^1$H NMR (300 MHz, DMSO-$d_6$) δ 7.48 (d, 1H), 6.90 (d, 1H), 5.51 (d, 1H), 4.66 (s, 1H), 3.65-3.74 (m, 1H), 2.21 (s, 1H), 2.01-2.13 (m, 1H), 1.50-1.78 (m, 5H), 1.07 (s, 3H). LC-ES/MS m/z 265.2 (M+1).

Example 2B

2-Chloro-4-[[(1S,2R)-2-hydroxy-2-methyl-cyclopentyl]amino]-3-methyl-benzonitrile

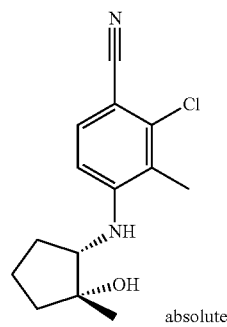 [SMILES: Cc1c(N[C@H]2CCC[C@@]2(C)O)ccc(C#N)c1Cl]

absolute

Cis-2-chloro-4-[[2-hydroxy-2-methyl-cyclopentyl]amino]-3-methyl-benzonitrile (9.5 g) is purified in 70 mg injections by supercritical fluid chromatography on two CHIRALPAK® Chiralpak AS-H columns (2×25 cm, 5 μm) stringed in series eluting with 20% ethanol/carbon. Flow rate: 65 mL/min. Detection: 215 nm. Each run is 4.5 min. The first eluting peak provides the title compound as Isomer 1 (4.23 g, >98% enantiomeric excess). Isomer 1 (title compound): $T_R$=1.40 min; Isomer 2: $T_R$=1.77 min. The absolute stereochemistry of Isomer 1 (1S,2R) is known by correlation of retentions times with Isomer 1 and Isomer 2 as described in Example 3.

The material obtained from SFC purification is dissolved in MTBE (10 L/Kg) and then treated with charcoal (200 mg) and silica gel (1 g). The mixture is stirred for 1 h and then filtered through a pad of diatomaceous earth. The filtrates are collected and evaporated to obtain the title compound (4.1 g) as a white solid. LC-ES/MS m/z 265.2 (M+1); $^1$H NMR (400 MHz, DMSO-$d_6$) δ 1.16 (s, 3H), 1.73-1.71 (m, 5H), 2.13-2.12 (m, 1H), 2.14 (s, 3H), 3.50-3.46 (m, 1H), 4.93 (s, 1H), 5.30-5.26 (m, 1H), 6.63 (d, J=8.8 Hz, 1H), 7.47 (d, J=8.6 Hz, 1H); Chiral purity ≥98% ee, Chiralpak AS-H, 20% EtOH/$CO_2$, 65 mL/min, 215 nm.

Example 3

2-Chloro-4-[[(1R,2S)-2-hydroxy-2-methyl-cyclopentyl]amino]-3-methyl-benzonitrile

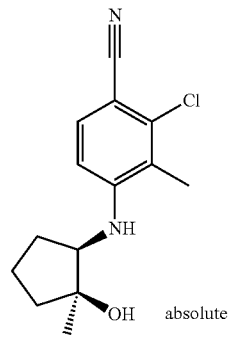 [SMILES: Cc1c(N[C@@H]2CCC[C@]2(C)O)ccc(C#N)c1Cl]

absolute

2-Chloro-4-[[2-hydroxy-2-methyl-cyclopentyl]amino]-3-methyl-benzonitrile is prepared essentially as described in Example 1 using 2-amino-1-methyl-cyclopentanol, hydrochloride and 2-chloro-4-fluoro-3-methyl-benzonitrile. The crude material was purified using silica gel chromatography (25-55% EtOAc/hexane) to obtain Diastereomer 1 (0.54 g) and Diastereomer 2 (1.56 g). Diastereomer 2 is assigned trans configuration based on co-crystal with AR.

Diastereomer 1 (cis-2-chloro-4-[[(2-hydroxy-2-methyl-cyclopentyl]amino]-3-methyl-benzonitrile) (500 mg) is dissolved in 5:1 methanol/dichloromethane (6 mL). The enantiomers are separated in 750 μL injections by supercritical fluid chromatography on a CHIRALPAK® AD-H column (2.1×25 cm). Mobile phase: 20% ethanol/carbon dioxide. Flow rate: 70 mL/min. Detection: 280 nm. Each run is 3.1 min. The first eluting peak is obtained as Isomer 1 (206 mg, 99% enantiomeric excess). The absolute stereochemistry of Isomer 1 (1S, 2R) is determined by X-ray of AR co-crystal.

The second eluting peak is obtained as the title compound (1R,2S), Isomer 2 (256 mg, 99% enantiomeric excess). The enantiomeric excess is determined by SFC on a CHIRALPAK® AD-H (2.1×25 cm, 5 μm) column using 20% ethanol/carbon dioxide. Flow rate: 5 mL/min. Detection: 225 nm. Isomer 1 $T_R$=1.37 min; Isomer 2 $T_R$=1.86 min. LC-ES/MS m/z 264.8 (M+1).

Example 4 and Example 5 cis-2-Chloro-4-[[2-hydroxy-2-methyl-cyclohexyl]amino]-3-methyl-benzonitrile and trans-2-Chloro-4-[[2-hydroxy-2-methyl-cyclohexyl]amino]-3-methyl-benzonitrile

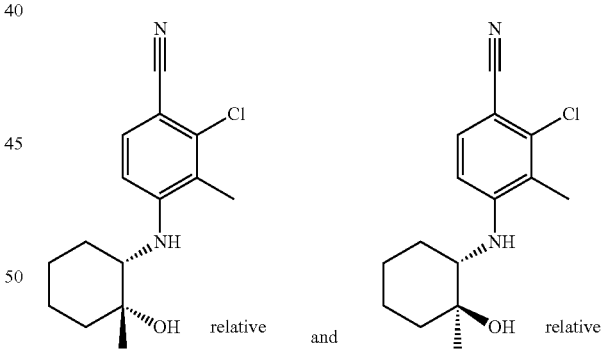

2-Chloro-4-[2-hydroxy-2-methyl-cyclopentyl]amino]-3-methyl-benzonitrile is prepared essentially as described in Example 1 using 2-amino-1-methyl-cyclohexanol hydrochloride and 2-chloro-4-fluoro-3-methyl-benzonitrile. The crude material was purified using silica gel chromatography (25-55% EtOAc/hexane) to obtain the first eluting compound as Diastereomer 1 (cis) (482 mg). LC-ES/MS m/z 279 (M+1) and The second eluting compound as Diastereomer 2 (trans) (101 mg). LC-ES/MS m/z 279 (M+1). Relative stereochemistry is assigned based on NMR of Example 6.

Examples 6 and 7

2-chloro-4-[[(1R,2S)-2-hydroxy-2-methyl-cyclohexyl]amino]-3-methyl-benzonitrile (Enantiomer 1) and 2-chloro-4-[[(1S,2R)-2-hydroxy-2-methyl-cyclohexyl]amino]-3-methyl-benzonitrile (Enantiomer 2)

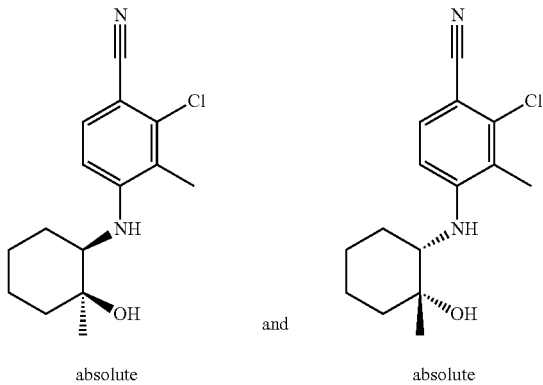 [SMILES: Cc1c(N[C@@H]2CCCC[C@]2(C)O)ccc(C#N)c1Cl ; Cc1c(N[C@H]2CCCC[C@@]2(C)O)ccc(C#N)c1Cl]

The enantiomeric mixture of cis-2-chloro-4-[[2-hydroxy-2-methyl-cyclohexyl]amino]-3-methyl-benzonitrile (450 mg) is dissolved in 2:1:1 methanol/ethanol/dichloromethane (4 mL) and separated in 300 μL injections by supercritical fluid chromatography on a CHIRALPAK® AD-H column (2.1×15 cm, 5 μm). Mobile phase: 20% ethanol/carbon dioxide. Flow rate: 70 mL/min. Detection: 225 nm. The first eluting peak is obtained as Enantiomer 1 and the second eluting peak is obtained as Enantiomer 2. The enantiomeric excess is determined by SFC on a CHIRALPAK® AD-H (2.1×25 cm, 5 μm) column using 20% ethanol/carbon dioxide. Flow rate: 5 mL/min. Detection: 225 nm.

Example 6

Enantiomer 1

216 mg, $T_R$=1.44 min, 99% ee; LC-ES/MS m/z 279 (M+1); Cis relative stereochemistry determined by NMR. $^1$H NMR (400 MHz, CDCl$_3$) δ 1.10-1.90 (m, 12H), 2.19 (s, 3H), 3.10-3.25 (m, 1H), 4.66 (d, 1H), 6.40 (d, 1H), 7.31 (d, 1H).

Example 7

Enantiomer 2

205 mg, $T_R$=1.83 min, 99% ee; LC-ES/MS m/z 279 (M+1). Absolute stereochemistry (1S,2R) determined by X-ray with AR.

Example 8

2-chloro-3-ethyl-4-[[(1S,2R)-2-hydroxy-2-methyl-cyclopentyl]amino]benzonitrile

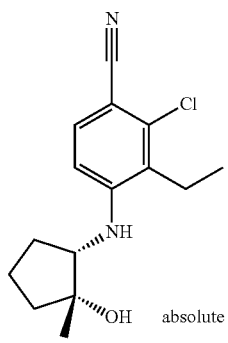 [SMILES: CCc1c(N[C@H]2CCC[C@@]2(C)O)ccc(C#N)c1Cl]

2-Chloro-3-ethyl-4-[[(1S)-2-hydroxy-2-methyl-cyclopentyl]amino]benzonitrile is prepared essentially as described in Example 1 using (2S)-2-amino-1-methyl-cyclopentanol hydrochloride (Preparation 18) and 2-chloro-3-ethyl-4-fluoro-benzonitrile. The crude material (350 mg) is purified using silica gel chromatography (20-60% EtOAc/hexane) to obtain Diastereomer 1 (cis) (82 mg) and Diastereomer 2 (trans) (29 mg).

Example 8

Diasteromer 1

LC-ES/MS m/z 279 (M+1). NMR analysis shows structure consistent with cis diastereomer. $^1$H-NMR (400 MHz, CDCl$_3$) δ 7.33 (d, J=8.7 Hz, 1H), 6.45 (d, J=8.8 Hz, 1H), 5.15-5.11 (m, 1H), 3.49-3.41 (m, 1H), 2.76-2.70 (m, 2H), 2.28-2.24 (m, 1H), 1.89-1.84 (m, 3H), 1.72-1.67 (m, 3H), 1.36 (s, 3H), 1.14 (t, J=7.6 Hz, 3H). The enantiomeric excess is determined by SFC on a CHIRALPAK® AS-H (2.1×25 cm) column using 20% EtOH/carbon dioxide. Flow rate: 5 mL/min. Detection: 225 nm. 70% ee, 85% @ $T_R$=1.24 min, 15% @ $T_R$=1.75 min.

Diasteromer 2:

LC-ES/MS m/z 279 (M+1). Chiral LC shows 60% ee.

The compounds in Table 5 below are prepared by essentially following the procedure as described for Example 1, using trans-4-aminotetrahydropyran-3-ol (Preparation 23) and 2-chloro-4-fluoro-3-methyl-benzonitrile or 2-chloro-3-ethyl-4-fluoro-benzonitrile.

TABLE 5

| Ex or Prep | Chemical name | Structure | LC-ES/MS m/z |
|---|---|---|---|
| 9 | trans-2-Chloro-4-[(3-hydroxytetrahydropyran-4-yl)amino]-3-methyl-benzonitrile | 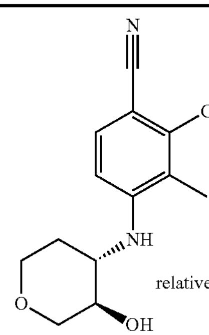 | 266.8 (M + 1) |
| Prep 45 | trans-2-Chloro-4-[(3-hydroxytetrahydropyran-4-yl)amino]-3-ethyl-benzonitrile | 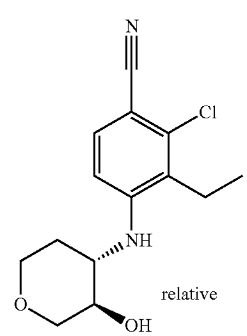 [SMILES: CCc1c(N[C@H]2CCOC[C@@H]2O)ccc(C#N)c1Cl] | 281.0 (M + 1) |

Example 10 cis-2-Chloro-3-ethyl-4-[[4-hydroxy-4-methyl-tetrahydrofuran-3-yl]amino]benzonitrile

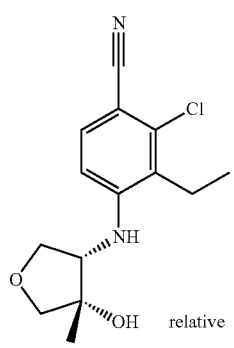 [SMILES: CCc1c(N[C@H]2COC[C@@]2(C)O)ccc(C#N)c1Cl] relative

The title compound is prepared by essentially following the procedure as described in Example 1, using cis-4-amino-3-methyl-tetrahydrofuran-3-ol hydrochloride (Preparation 30) and 2-chloro-3-ethyl-4-fluoro-benzonitrile. NMR analysis in comparison with Example 1 and 2 indicates cis relative stereochemistry. $^1$H-NMR (400 MHz, CDCl$_3$) δ 7.36-7.33 (m, 1H), 6.37 (d, J=8.7 Hz, 1H), 5.30-5.25 (m, 1H), 4.30-4.26 (m, 1H), 3.87 (d, J=9.9 Hz, 1H), 3.78-3.74 (m, 2H), 3.64-3.59 (m, 1H), 2.76 (q, J=7.6 Hz, 2H), 2.13 (s, 1H), 1.44-1.43 (m, 3H), 1.16 (t, J=7.6 Hz, 3H). LC-ES/MS m/z 281 (M+1).

Example 11 trans-2-Chloro-3-ethyl-4-[[4-hydroxy-4-methyl-tetrahydrofuran-3-yl]amino]benzonitrile

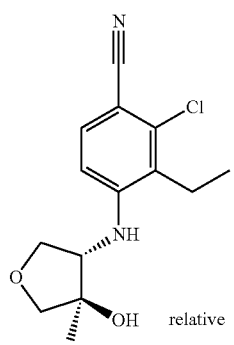 [SMILES: CCc1c(N[C@H]2COC[C@]2(C)O)ccc(C#N)c1Cl] relative

The title compound is prepared by essentially following the procedure as described in Example 1, using trans-4-amino-3-methyl-tetrahydrofuran-3-ol hydrochloride (Preparation 29) and 2-chloro-3-ethyl-4-fluoro-benzonitrile. NMR analysis in comparison with Example 1 and 2 indicates trans relative stereochemistry. $^1$H-NMR (400 MHz, CDCl$_3$) δ 7.36 (d, J=8.6 Hz, 1H), 6.71 (d, J=8.8 Hz, 1H), 4.45 (dd, J=6.2, 9.6 Hz, 1H), 4.27-4.24 (m, 1H), 4.03-3.98 (m, 1H), 3.84 (d, J=9.8 Hz, 1H), 3.71 (d, J=9.8 Hz, 1H), 3.62 (dd, J=4.1, 9.6 Hz, 1H), 2.81-2.70 (m, 2H), 2.35-2.34 (m, 1H), 1.32 (s, 3H), 1.13 (t, J=7.6 Hz, 3H). LC-ES/MS m/z 281 (M+1).

Example 12

2-Chloro-4-[[(3R,4R)-4-hydroxytetrahydrofuran-3-yl]amino]-3-methyl-benzonitrile

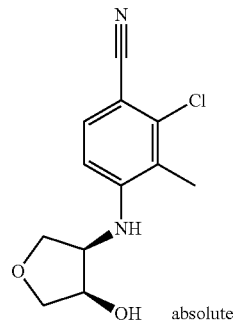 [SMILES: Cc1c(N[C@@H]2COC[C@@H]2O)ccc(C#N)c1Cl] absolute

The title compound is prepared by essentially following the procedure as described in Example 1 using (3R,4R)-4-(tert-butyl(dimethyl)silyl)oxytetrahydrofuran-3-amine (Preparation 36) and 2-chloro-4-fluoro-3-methyl-benzonitrile. The crude product is purified on silica gel using 40-70% EtOAc/hexanes. The isolated product is dissolved in THF to make a 0.5 M solution. TBAF (2.0 mL, 2 mmol, 1 M solution in THF) is added and stirred at room temperature for 16 h. The solution is concentrated in vacuo, EtOAc is added, and the solution is washed with water (2×). The organic portion is dried over magnesium sulfate, filtered, and concentrated. The residue is purified by reverse phase chromatography on silica-bound C18 using 15-95% acetonitrile/water+0.1% formic acid. Fractions containing the title compound are concentrated in vacuo to remove acetonitrile, then extracted with EtOAc. The organics are dried over magnesium sulfate and concentrated in vacuo to give the title compound as a white solid (134 mg, 19%). $^1$H-NMR (400 MHz, DMSO-d$_6$) δ 7.53 (d, J=8.7 Hz, 1H), 6.73 (d, J=8.8 Hz, 1H), 5.60-5.56 (m, 1H), 5.53 (d, J=4.9 Hz, 1H), 4.33-4.29 (m, 1H), 4.05-3.99 (m, 2H), 3.92 (dd, J=4.6, 9.6 Hz, 1H), 3.63 (dd, J=2.4, 9.5 Hz, 1H), 3.53-3.50 (m, 1H), 2.19 (s, 3H). LC-ES/MS m/z 253 (M+1).

The Examples in Table 6 below are prepared by essentially following the procedure described in Example 12 using the appropriate TMS or TBDMS-protected aminoalcohol and 2-chloro-4-fluoro-3-methyl-benzonitrile or 2-chloro-3-ethyl-4-fluoro-benzonitrile.

TABLE 6

| Ex | Chemical name | Structure | LC-ES/MS m/z |
|---|---|---|---|
| 13 | 2-Chloro-4-[[(3S,4R)-4-hydroxytetrahydrofuran-3-yl]amino]-3-methyl-benzonitrile | absolute | 253 (M + 1) |

TABLE 6-continued

| Ex | Chemical name | Structure | LC-ES/MS m/z |
|---|---|---|---|
| 14 | 2-Chloro-4-[[(3R,4S)-4-hydroxytetrahydrofuran-3-yl]amino]-3-methyl-benzonitrile | 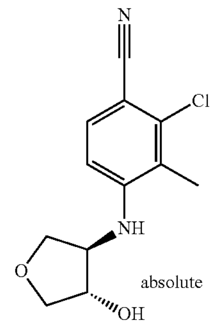 [SMILES: Cc1c(N[C@@H]2COC[C@H]2O)ccc(C#N)c1Cl] | 253 (M+1) |
| 15 | 2-Chloro-3-ethyl-4-[[(3R,4R)-4-hydroxytetrahydrofuran-3-yl]amino]benzonitrile | 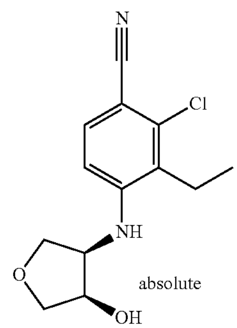 [SMILES: CCc1c(N[C@@H]2COC[C@@H]2O)ccc(C#N)c1Cl] | 267 (M+1) |

Preparation 46

2-Chloro-3-methyl-4-[(3-oxotetrahydropyran-4-yl)amino]benzonitrile

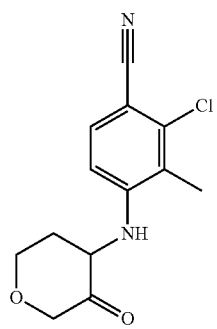 [SMILES: Cc1c(NC2CCOCC2=O)ccc(C#N)c1Cl]

To a solution of oxalyl chloride (1.22 mL, 14.1 mmol) in dichloromethane (15 mL) at −60° C. is added dropwise a solution of dimethyl sulfoxide (2.08 mL, 29.3 mmol) in dichloromethane (15 mL) and stirred at −60° C. for 15 min. trans-2-chloro-4-[(3-hydroxytetrahydropyran-4-yl)amino]-3-methyl-benzonitrile (3.13 g, 11.7 mmol, Example 9) in dichloromethane (30 mL) is added to the solution and stirred at −60° C. for 30 min. Triethylamine (9 mL, 64.5 mmol) is added and the mixture is warmed to room temperature and stirred for 3 h. The mixture is diluted with EtOAc and washed twice with 1 N hydrochloric acid. The organic portion is dried over sodium sulfate, filtered, and concentrated in vacuo to give the crude title compound as an orange semi-solid (2.53 g, 81%). LC-ES/MS m/z 265.2 (M+1).

The oxotetrahydropyran or oxotetrahydrofurans in Table 7 below, are prepared by essentially following the procedure described in Preparation 46, using as starting material the appropriate alcohol and proceeding with 1.2 to 1.5 eq oxalyl chloride, and 2.5 to 3 eq of DMSO, at −60 to −75° C. in THF.

TABLE 7

| Prep | Chemical name | Structure | LC-ES/MS m/z |
|---|---|---|---|
| 47 | 2-Chloro-3-ethyl-4-[(3-oxotetrahydropyran-4-yl)amino]benzonitrile | 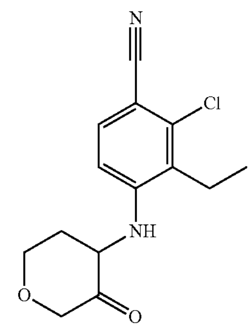 [SMILES: CCc1c(NC2CCOCC2=O)ccc(C#N)c1Cl] | 278.8 (M+1) |
| 48 | 2-Chloro-3-methyl-4-[[(3S)-4-oxotetrahydrofuran-3-yl]amino]benzonitrile | 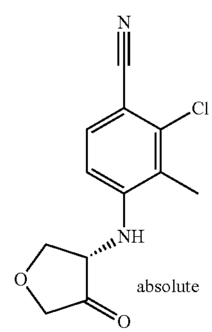 [SMILES: Cc1c(N[C@H]2COCC2=O)ccc(C#N)c1Cl] | 249 (M−1) |
| 49 | 2-Chloro-3-methyl-4-[[(3R)-4-oxotetrahydrofuran-3-yl]amino]benzonitrile | 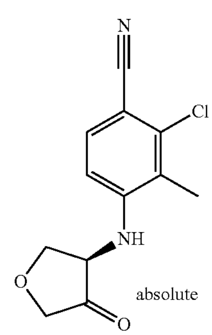 [SMILES: Cc1c(N[C@@H]2COCC2=O)ccc(C#N)c1Cl] | 251 (M+1) |

Examples 16 and 17

2-chloro-4-[[(3S,4S)-4-hydroxy-4-methyl-tetrahydrofuran-3-yl]amino]-3-methyl-benzonitrile and 2-chloro-4-[[(3S,4R)-4-hydroxy-4-methyl-tetrahydrofuran-3-yl]amino]-3-methyl-benzonitrile

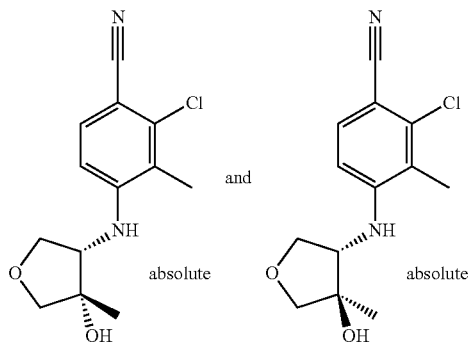 [SMILES: Cc1c(N[C@H]2COC[C@@]2(C)O)ccc(C#N)c1Cl ; Cc1c(N[C@H]2COC[C@]2(C)O)ccc(C#N)c1Cl]

A solution of 2-chloro-3-methyl-4-[[(3S)-4-oxotetrahydrofuran-3-yl]amino]benzonitrile (148 mg, 0.590 mmol) in THF (2.4 mL) at 0° C. is treated with methylmagnesium bromide (0.49 mL, 1.50 mmol, 3 M in diethyl ether) dropwise under nitrogen. The reaction is warmed up to room temperature and stirred for 16 h. The reaction is quenched with saturated aqueous ammonium chloride (5 mL) and extracted with EtOAc (3×40 mL). The combined organics are dried over magnesium sulfate, filtered, and concentrated to give 143 mg of crude product. The crude product is purified on silica gel (24 g, 5-80% EtOAc/hexanes) to give the title compounds.

Example 16

3S,4S-isomer

First to elute from the column is the 3S,4S-isomer which is isolated as a yellow film (25 mg, 16%). Its diastereomerism and thus absolute stereochemistry is determined by NMR analysis. $^1$H-NMR (400 MHz, CDCl$_3$) δ 7.35 (d, J=8.6 Hz, 1H), 6.37 (d, J=8.6 Hz, 1H), 5.10 (d, J=7.0 Hz, 1H), 4.28 (dd, J=7.1, 9.0 Hz, 1H), 3.88 (d, J=9.9 Hz, 1H), 3.77 (dt, J=9.9, 5.6 Hz, 2H), 3.62 (dd, J=7.0, 9.0 Hz, 1H), 2.34-2.30 (m, 1H), 2.25 (s, 3H), 1.44 (s, 3H). LC-ES/MS m/z 267 (M+1).

Example 17

3S,4R-isomer

Second to elute from the column is the 3S,4R-isomer which is isolated as a tan film (48 mg, 30%). $^1$H-NMR (400 MHz, CDCl$_3$) δ 7.40-7.38 (m, 1H), 6.72-6.70 (m, 1H), 4.48-4.44 (m, 1H), 4.14-4.13 (m, 1H), 4.06-4.04 (m, 1H), 3.86-3.83 (m, 1H), 3.72 (d, J=9.8 Hz, 1H), 3.64-3.59 (m, 1H), 2.23 (s, 3H), 2.14 (s, 1H), 1.31 (s, 3H). LC-ES/MS m/z 267 (M+1).

Examples 18 and 19

2-chloro-4-[[(3R,4R)-4-hydroxy-4-methyl-tetrahydrofuran-3-yl]amino]-3-methyl-benzonitrile and 2-chloro-4-[[(3R,4S)-4-hydroxy-4-methyl-tetrahydrofuran-3-yl]amino]-3-methyl-benzonitrile

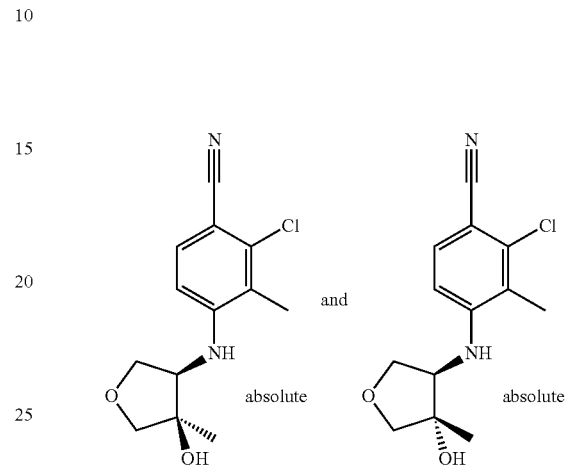

The title compounds are prepared by essentially following the procedure as described for Examples 16 and 17, using 2-chloro-3-methyl-4-[[(3R)-4-oxotetrahydrofuran-3-yl]amino]benzonitrile. The crude product is purified on silica gel (5-80% EtOAc/hexanes).

Example 18

3R,4R-isomer

First isomer to elute from the column is the 3R,4R-isomer which is isolated as a white solid (60 mg, 7%). Its diastereomerism and thus absolute stereochemistry is determined by NMR analysis. $^1$H-NMR (400 MHz, CDCl$_3$) δ 7.35 (d, J=8.6 Hz, 1H), 6.37 (d, J=8.6 Hz, 1H), 5.25-5.24 (m, 1H), 4.28 (dd, J=7.1, 9.0 Hz, 1H), 3.88 (d, J=9.9 Hz, 1H), 3.79-3.75 (m, 2H), 3.62 (dd, J=6.9, 9.0 Hz, 1H), 2.26 (s, 3H), 1.44 (s, 3H). LC-ES/MS m/z 267 (M+1).

Example 19

3R,4S-isomer

Second isomer to elute from the column is the 3R,4S-isomer which is isolated as a white solid (115 mg, 13%). $^1$H-NMR (400 MHz, CDCl$_3$) δ 7.38 (d, J=8.6 Hz, 1H), 6.71 (d, J=8.7 Hz, 1H), 4.45 (dd, J=6.2, 9.6 Hz, 1H), 4.14-4.09 (m, 1H), 4.04-3.99 (m, 1H), 3.84 (d, J=9.9 Hz, 1H), 3.71 (d, J=9.8 Hz, 1H), 3.63-3.60 (m, 1H), 2.23 (s, 3H), 2.04 (s, 1H), 1.31 (s, 3H). LC-ES/MS m/z 267 (M+1).

Examples 20 and 21

2-Chloro-4-[[(1S,2R,3S)-2,3-dihydroxy-2-methyl-cyclopentyl]amino]-3-methyl-benzonitrile (Isomer 1) and 2-Chloro-4-[[(1R,2S,3R)-2,3-dihydroxy-2-methyl-cyclopentyl]amino]-3-methyl-benzonitrile (Isomer 2)

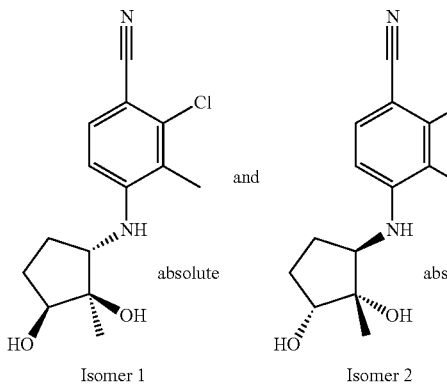

Isomer 1    Isomer 2

The TBDPS-protected title compound is prepared by essentially following the procedure described in Example 1, using rel-(1S,2R,5R)-2-amino-5-(tert-butyl(diphenyl)silyl)oxy-1-methyl-cyclopentanol (9.84 g, 26.62 mmol, Preparation 44) and 2-chloro-4-fluoro-3-methyl-benzonitrile (3.42 g, 20.17 mmol). A 0.2 M solution of the crude product in THF is treated with TBAF (30.25 mL, 30.25 mmol, 1.0 M in THF) and stirred at room temperature for 16 h. The mixture is treated with water, concentrated in vacuo and extracted into EtOAc. The organic extracts are dried over magnesium sulfate, filtered, and concentrated. The resulting residue is purified on silica gel (25-75% EtOAc/hexanes) to give the racemic title compound as a pale yellow solid (3.27 g, 58%). NMR analysis indicates the relative stereochemistry shown. $^1$H-NMR (400 MHz, DMSO-d$_6$) δ 7.48 (d, J=8.8 Hz, 1H), 6.89 (d, J=8.8 Hz, 1H), 5.60-5.58 (m, 1H), 4.74 (d, J=5.4 Hz, 1H), 4.27 (s, 1H), 3.82-3.80 (m, 1H), 3.55-3.53 (m, 1H), 3.29 (s, 1H), 3.15 (d, J=5.2 Hz, 1H), 2.20 (s, 3H), 2.04-2.01 (m, 1H), 1.86-1.84 (m, 1H), 1.64-1.61 (m, 2H), 0.95 (s, 3H). LC-ES/MS m/z 281 (M+1).

The compound is dissolved in isopropanol and chloroform (2:1). The enantiomers are separated in 150 mg injections by supercritical fluid chromatography on a CHIRALPAK® AD-H column (0.5×1.5 cm). Mobile phase: 30% isopropanol/carbon dioxide. Flow rate: 300 mL/min. Detection: 290 nm. The first eluting peak is obtained as Isomer 1 and the second eluting peak is obtained as Isomer 2. The enantiomeric excess is determined by SFC on a CHIRALPAK® AD-H (4.6×100 mm) column using 20% isopropanol/carbon dioxide. Detection: 215 nm.

Example 20

Isomer 1-1S,2R,3S

Isolated as a white solid (1.5 g, 27%). T$_R$=1.80 min, >99% ee. LC-ES/MS m/z 281 (M+1).

Example 21

Isomer 2-1R,2S,3R

Isolated as a white solid (1.4 g, 25%). T$_R$=2.75 min, >99% ee. LC-ES/MS m/z 281 (M+1). The absolute stereochemistry (1R,2S,3R) of Isomer 2 is determined by X-ray of AR co-crystal as depicted above for the drawing of Example 21.

Example 22 rel-2-Chloro-4-[[(1R,2S,3S)-2,3-dihydroxy-2-methyl-cyclopentyl]amino]-3-methyl-benzonitrile

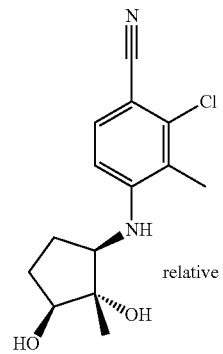 [SMILES: Cc1c(N[C@@H]2CC[C@H](O)[C@@]2(C)O)ccc(C#N)c1Cl]

The title compound is prepared by essentially following the procedure described in Example 1, using rel-(1S,2R,5 S)-2-amino-5-(tert-butyl(diphenyl)silyl)oxy-1-methyl-cyclopentanol (409 mg, 1.1 mmol, Preparation 43) and 2-chloro-4-fluoro-3-methyl-benzonitrile (142 mg, 0.84 mmol). A 0.2 M solution of the crude product in THF is treated with tetrabutylammonium fluoride (1.3 mL, 1.3 mmol, 1.0 M in THF) and stirred at room temperature for 16 h. The mixture is treated with water, concentrated in vacuo and extracted with EtOAc. The organic extracts are dried over magnesium sulfate, filtered, and concentrated. The resulting material is purified on silica gel (25-100% EtOAc/hexanes) to give the title compound as a pale yellow oil (15 mg, 6%). The relative stereochemistry is determined by NMR studies. $^1$H-NMR (400 MHz, DMSO-d$_6$) δ 7.47 (d, J=8.8 Hz, 1H), 6.78 (d, J=8.8 Hz, 1H), 5.60-5.57 (m, 1H), 4.98 (d, J=4.2 Hz, 1H), 4.68 (s, 1H), 3.73-3.70 (m, 2H), 2.12 (s, 3H), 2.09-2.09 (m, 2H), 1.69-1.67 (m, 1H), 1.52-1.49 (m, 1H), 1.07 (s, 3H). LC-ES/MS m/z 281 (M+1).

Example 23 rel-2-Chloro-4-[[(1R,2S,3R)-2,3-dihydroxy-2-methyl-cyclopentyl]amino]-3-ethyl-benzonitrile

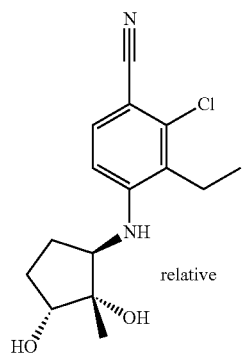 [SMILES: CCc1c(N[C@@H]2CC[C@@H](O)[C@@]2(C)O)ccc(C#N)c1Cl]

The title compound is prepared by essentially following the procedure described in Example 20, using rel-(1S,2R,5R)-2-amino-5-(tert-butyl(diphenyl)silyl)oxy-1-methyl-cyclopentanol and 2-chloro-3-ethyl-4-fluoro-benzonitrile for the substitution reaction followed by TBDPS removal with TBAF. $^1$H-NMR (400 MHz, DMSO-d$_6$) δ 7.44 (d, J=8.7 Hz, 1H), 6.87 (d, J=9.0 Hz, 1H), 5.74-5.70 (m, 1H), 4.74 (d, J=5.4 Hz, 1H), 4.27 (s, 1H), 3.82-3.79 (m, 1H), 3.58-3.51 (m, 1H), 2.80-2.78 (m, 2H), 2.03-2.02 (m, 1H), 1.88-1.86 (m, 1H), 1.69-1.68 (m, 1H), 1.52-1.51 (m, 1H), 1.01-0.97 (m, 3H), 0.93 (s, 3H). LC-ES/MS m/z 295 (M+1).

Example 24

2-Chloro-4-[[(1R,2S)-2-hydroxycyclohexyl]amino]-3-methyl-benzonitrile

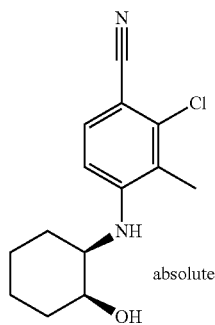 [SMILES: Cc1c(N[C@@H]2CCCC[C@@H]2O)ccc(C#N)c1Cl]

A mixture of 2-chloro-4-fluoro-3-methyl-benzonitrile (500 mg, 2.95 mmol), diisopropylethylamine (1.29 mL, 7.37 mmol), and (1S,2R)-2-aminocyclohexanol hydrochloride (670 mg, 4.42 mmol, Acros®) is microwaved using a CEM® microwave at 190° C. for 2 h and 180° C. for 4 h. The mixture is diluted with dichloromethane and washed with 1 N HCl. The aqueous layer is extracted again with dichloromethane. The combined organic phases are dried over sodium sulfate, filtered, and concentrated in vacuo. The resulting residue is purified using radial chromatography, eluting with 2% methanol/dichloromethane. The isolated product is recrystallized with ether and hexane to yield the title compound as a white solid (231 mg, 29%). LC-ES/MS m/z 265.0 (M+1).

The compounds in Table 8 below are prepared by essentially following the procedure described in Example 24, using the appropriate chiral amino-alcohol (commercially available) and 2-chloro-4-fluoro-3-methyl-benzonitrile.

TABLE 8

| Ex | Chemical name | Structure | LC-ES/MS m/z |
|---|---|---|---|
| 25 | 2-Chloro-4-[[(1S,2S)-2-hydroxycyclohexyl]amino]-3-methyl-benzonitrile | | 265.0 (M + 1) |
| 26 | 2-Chloro-4-[[(1S,2R)-2-hydroxycyclopentyl]amino]-3-methyl-benzonitrile | 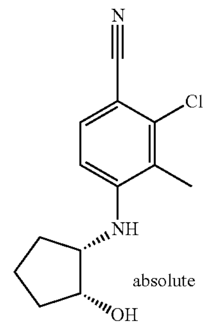 [SMILES: Cc1c(N[C@H]2CCC[C@H]2O)ccc(C#N)c1Cl] | 251.2 (M + 1) |
| 27 | 2-Chloro-4-[[(1R,2S)-2-hydroxycyclopentyl]amino]-3-methyl-benzonitrile | 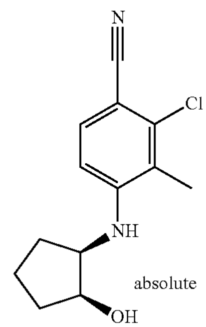 [SMILES: Cc1c(N[C@@H]2CCC[C@@H]2O)ccc(C#N)c1Cl] | 251.2 (M + 1) |

Example 28

2-Chloro-4-[[(1S,2R)-2-hydroxycyclohexyl]amino]-3-methyl-benzonitrile

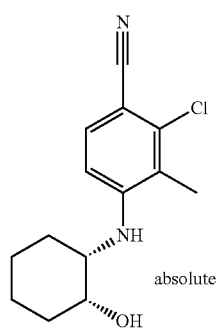 [SMILES: Cc1c(N[C@H]2CCCC[C@H]2O)ccc(C#N)c1Cl]

A solution of 2-chloro-4-fluoro-3-methyl-benzonitrile (500 mg, 2.95 mmol), (1R,2S)-2-aminocyclohexanol hydrochloride (671 mg, 4.42 mmol, Small Molecules, Inc.) and sodium bicarbonate (991 mg, 11.8 mmol) in DMSO (14.7 mL), and water (2.1 mL) is heated at 130° C. for 48 h. After cooling to room temperature, the mixture is diluted with 1 N HCl and extracted twice with EtOAc. The organic layers are combined, dried over sodium sulfate, filtered, and concentrated in vacuo. The resulting residue is purified using radial chromatography, eluting with 2% methanol/dichloromethane to furnish the title compound as an off-white solid (527 mg, 68%). LC-ES/MS m/z 265.2 (M+1).

Example 29 and 30

2-Chloro-4-[[3-hydroxy-3-methyl-tetrahydropyran-4-yl]amino]-3-methyl-benzonitrile, Diastereomer 1 and 2-Chloro-4-[[3-hydroxy-3-methyl-tetrahydropyran-4-yl]amino]-3-methyl-benzonitrile, Diastereomer 2

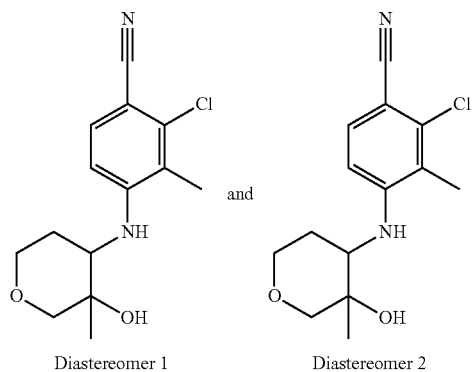 [SMILES: Cc1c(NC2CCOCC2(C)O)ccc(C#N)c1Cl ; Cc1c(NC2CCOCC2(C)O)ccc(C#N)c1Cl]

Diastereomer 1          Diastereomer 2

To a solution 2-chloro-3-methyl-4-[(3-oxotetrahydropyran-4-yl)amino]benzonitrile (2.53 g, 9.56 mmol, Preparation 46) in THF (38 mL) at 0° C. is added methylmagnesium bromide (9.56 mL, 28.7 mmol, 3 M in diethyl ether) and the reaction is allowed to warm to room temperature. After 1 h, the reaction is quenched with saturated aqueous ammonium chloride. EtOAc is added and the mixture is washed with water. The organic portion is dried with sodium sulfate, filtered, and concentrated in vacuo. The resulting residue is purified using silica gel chromatography eluting with 5% MeOH/dichloromethane. The resulting material is repurified with 2% MeOH/dichloromethane, then again with 1.5% MeOH/dichloromethane to separate the diastereomers. Each product is recrystallized using dichloromethane and ether to yield the title products.

Example 29

Diastereomer 1

Isolated as an off-white solid (549 mg, 21%). The relative stereochemistry is unknown. $^1$H-NMR (400 MHz, DMSO-$d_6$) δ 7.47 (d, J=8.7 Hz, 1H), 6.74-6.72 (m, 1H), 5.04-5.00 (m, 1H), 4.95 (s, 1H), 3.80-3.75 (m, 1H), 3.58-3.54 (m, 2H), 3.42-3.38 (m, 1H), 3.26 (d, J=7.6 Hz, 1H), 2.15 (s, 3H), 1.72-1.69 (m, 2H), 0.94 (s, 3H). LC-ES/MS m/z 281.2 (M+1).

Example 30

Diastereomer 2

Isolated as an off-white solid (300 mg, 11%). The relative stereochemistry is unknown. $^1$H-NMR (400 MHz, DMSO-$d_6$) δ 7.42 (d, J=8.7 Hz, 1H), 6.94 (d, J=9.0 Hz, 1H), 5.28-5.24 (m, 1H), 4.68 (s, 1H), 3.82-3.78 (m, 1H), 3.61-3.60 (m, 1H), 3.40 (d, J=10.9 Hz, 1H), 3.35-3.31 (m, 1H), 3.09 (d, J=11.0 Hz, 1H), 2.19 (s, 3H), 1.77-1.75 (m, 2H), 1.11 (s, 3H). LC-ES/MS m/z 281.2 (M+1).

Example 31 and 32

2-Chloro-3-ethyl-4-[[3-hydroxy-3-methyl-tetrahydropyran-4-yl]amino]benzonitrile, Diastereomer 1 and 2-Chloro-3-ethyl-4-[[3-hydroxy-3-methyl-tetrahydropyran-4-yl]amino]benzonitrile, Diastereomer 2

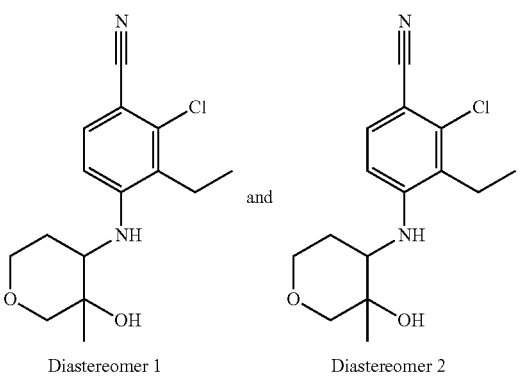 [SMILES: CCc1c(NC2CCOCC2(C)O)ccc(C#N)c1Cl ; CCc1c(NC2CCOCC2(C)O)ccc(C#N)c1Cl]

Diastereomer 1          Diastereomer 2

The title compounds are prepared as racemic diastereomers in a manner analogous to the preparation found in Examples 29 and 30. The diastereomers are separated using silica gel chromatography eluting with 1.5% MeOH/dichloromethane. The diastereomers are further purified and separated using silica gel chromatography eluting with 10% acetone/dichloromethane.

Example 31

Diastereomer 1

Isolated as an off-white solid (551 mg, 19%). The relative stereochemistry is unknown. $^1$H-NMR (400 MHz, DMSO-$d_6$) δ 7.47-7.45 (m, 1H), 6.76-6.73 (m, 1H), 5.16-5.14 (m, 1H), 5.04-4.99 (m, 1H), 3.84-3.81 (m, 1H), 3.60-3.58 (m, 2H), 3.43-3.42 (m, 1H), 3.26-3.23 (m, 1H), 2.71-2.70 (m, 2H), 1.72-1.70 (m, 2H), 1.12-1.02 (m, 3H), 0.95 (s, 3H). LC-ES/MS m/z 295.0 (M+1).

Example 32

Diastereomer 2

Isolated as an off-white solid (392 mg, 13%). The relative stereochemistry is unknown. $^1$H-NMR (400 MHz, DMSO-$d_6$) δ 7.40 (d, J=8.9 Hz, 1H), 6.96 (d, J=9.1 Hz, 1H), 5.41-5.38 (m, 1H), 4.69 (s, 1H), 3.86-3.81 (m, 1H), 3.59-3.58 (m, 1H), 3.42-3.38 (m, 1H), 3.34-3.28 (m, 1H), 3.11-3.07 (m, 1H), 2.78-2.75 (m, 2H), 1.81-1.80 (m, 1H), 1.67-1.63 (m, 1H), 1.10 (s, 3H), 1.01 (t, J=7.4 Hz, 3H). LC-ES/MS m/z 295.0 (M+1).

Example 33 and 34

2-Chloro-3-ethyl-4-[[3-hydroxy-3-methyl-tetrahydropyran-4-yl]amino]benzonitrile, Isomer 1 and 2-Chloro-3-ethyl-4-[[3-hydroxy-3-methyl-tetrahydropyran-4-yl]amino]benzonitrile, Isomer 2

Example 32 (Diastereomer 2) is dissolved in 2:1 methanol/dichloromethane (9 mL) and separated in 1000 μL injections by supercritical fluid chromatography on a CHIRALPAK® AD-H column (2.1×15 cm, 5 μm). Mobile phase: 25% ethanol/carbon dioxide. Flow rate: 70 mL/min. Detection: 225 nm. Each run is 3.5 min. The first eluting peak is obtained as Isomer 1 and the second eluting peak is obtained as Isomer 2. The enantiomeric excess is determined by SFC on a CHIRALPAK® AD-H (2.1×15 cm, 5 μm) column using 25% ethanol/carbon dioxide. Flow rate: 5 mL/min. Detection: 225 nm.

Example 33

Isomer 1

Isolated as an off-white foam (256 mg, 49%). $T_R$=1.14 min, 99% ee.

Example 34

Isomer 2

Isolated as an off-white foam (221 mg, 42%) $T_R$=1.86 min, 99% ee. $^1$H-NMR (400 MHz, DMSO-d$_6$) δ 7.47-7.45 (m, 1H), 6.76-6.73 (m, 1H), 5.16-5.14 (m, 1H), 5.04-4.99 (m, 1H), 3.84-3.81 (m, 1H), 3.60-3.58 (m, 2H), 3.43-3.42 (m, 1H), 3.26-3.23 (m, 1H), 2.71-2.70 (m, 2H), 1.72-1.70 (m, 2H), 1.12-1.02 (m, 3H), 0.95 (s, 3H). LC-ES/MS m/z 295.0 (M+1).

Steroid Hormone Nuclear Receptor Binding Assay

Cell lysates from human embryonic kidney HEK293 cells overexpressing human MR (mineralocorticoid receptor), GR (glucocorticoid receptor), AR (androgen receptor), or PR (progesterone receptor) are used for receptor-ligand competition binding assays to determine $K_i$ values. Typical procedures are provided below.

Briefly, steroid receptor competition binding assays are run in a buffer containing 20 mM HEPES buffer (pH=7.6), 0.2 mM EDTA, 75 mM NaCl, 1.5 mM MgCl$_2$, 20% glycerol, 20 mM sodium molybdate, 0.2 mM DTT, 20 μg/mL aprotinin and 20 μg/mL leupeptin (assay buffer). Typically, steroid receptor binding assays include radio-labeled ligands, such as 0.25 nM [$^3$H]-aldosterone for MR binding, 0.3 nM [$^3$H]-dexamethasone for GR binding, 0.36 nM [$^3$H]-methyltrienolone for AR binding, and 0.29 nM [$^3$H]-methyltrienolone for PR binding, and either 20 μg 293-MR lysate, 20 μg 293-GR lysate, 22 μg 293-AR lysate, or 40 μg 293-PR lysate per well. Assays are typically run in 96-well format. Competing test compounds are added at various concentrations ranging from about 0.01 nM to 10 μM. Non-specific binding is determined in the presence of 500 nM aldosterone for MR binding, 500 nM dexamethasone for GR binding, or 500 nM methyltrienolone for AR and PR binding. The binding reactions (140 μL) are incubated overnight at 4° C., then 70 μL of cold charcoal-dextran buffer (containing per 50 mL of assay buffer, 0.75 g of charcoal and 0.25 g of dextran) is added to each reaction. Plates are mixed for 8 min on an orbital shaker at 4° C. The plates are then centrifuged at 3,000 rpm at 4° C. for 10 min. An aliquot of 120 μL of the binding reaction mixture is then transferred to another 96-well plate and 175 μL of Wallac Optiphase Hisafe 3™ scintillation fluid is added to each well. Plates are sealed and shaken vigorously on an orbital shaker. After an incubation of 2 h, plates are read in a Wallac MICROBETA® counter.

The data are used to calculate an estimated IC$_{50}$ and percentage inhibition at 10 μM. The Kd for [$^3$H]-aldosterone for MR binding, [$^3$H]-dexamethasone for GR binding, [$^3$H]-methyltrienolone for AR binding, or [$^3$H]-methyltrienolone for PR binding, is determined by saturation binding. The IC$_{50}$ values for compounds are converted to Ki using the Cheng-Prushoff equation.

The compounds of the Examples herein were tested essentially as described above and exhibited a Ki value for AR of lower than 1 μM. The following exemplified compounds of the invention were tested essentially as described above and exhibited the following affinity for AR as illustrated in Table 9 below.

TABLE 9

| Ex | AR (Ki nM) | GR (Ki nM) | MR (Ki nM) | PR (Ki nM) |
|---|---|---|---|---|
| 1 | 2.03 | >6020 | 1450 | 872 |
| 2 | 0.684 | 462 | 1840 | 448 |
| 5 | 16.9 | >3120 | 415 | 520 |
| 16 | 5.21 | 2390 | >7010 | 1220 |
| 20 | 38.1 | >5730 | >7150 | >7960 |
| 32 | 162 | >5820 | 3960 | 4290 |

The data in Table 9 show that the compounds of Table 9 are potent and selective ligands for the AR.

C2C12 AR/ARE Reporter Assay

As an indicator of agonist activity in muscle tissue, the C2C12 AR/ARE reporter assay is performed. Briefly, mouse myoblast C2C12 cells are co-transfected using Fugene™ reagent. A reporter plasmid containing a GRE/ARE (glucocorticoid response element/androgen response element) and TK promoter upstream of the luciferase reporter cDNA, is transfected with a plasmid constitutively expressing human androgen receptor (AR) using viral CMV promoter. Cells are transfected in T150 cm$^2$ flasks in DMEM media with 4% CS-FBS. After a 5 h incubation, transfected cells are trypsinized, plated in 96 well dishes in DMEM media containing 4% CS-FBS, incubated for 2 h and then exposed to various concentrations of test compounds ranging from about 0.01 nM to 10 μM. After 24 h of incubations with compounds, cells are lysed and luciferase activity is determined by standard techniques. Data is fit to a 4 parameter-fit logistics to determine EC$_{50}$ values. The % efficacy is determined versus maximum stimulation obtained with 10 nM methyltrienolone.

Functional assays of steroid hormone nuclear hormone receptor modulation similar to those described above can be readily designed by the ordinarily skilled artisan. The compounds of the Examples herein were tested essentially as described above as illustrated in Table 10 below.

TABLE 10

| Ex | AR C2C12 EC$_{50}$ (nM) |
|---|---|
| 1 | 0.499 (n = 10) |
| 2 | 0.0398 (n = 6) |
| 5 | 4.88 |
| 16 | 73.7 |
| 20 | 146 |
| 32 | 274 |

The data in Table 10 demonstrate that the compounds of Table 10 are an agonist of human AR.

In Vivo Model of Efficacy and Selectivity

Hypogonadism induced sarcopenia muscle atrophy can occur as a result of various disease conditions including aging, cancer cachexia, sepsis, denervation, disuse, inactivity, burns, HIV-acquired immunodeficiency syndrome (AIDS), chronic kidney or heart failure, unloading/microgravity, and muscular dystrophies etc. The sequence of events that leads to muscle loss under these various conditions is different, but collectively leads to an imbalance in muscle anabolic and muscle catabolic pathways, such that there is a net loss in muscle mass and function that can be measured in a delayed rat gonadectomy model via changes in Levator Ani (LA) muscle and Bulbo Cavernosus (BC) perineal muscle wet weights.

Male Sprague Dawley rats (8 weeks old) are castrated (gonadectomized or "GDX") according to approved procedures (Charles River Labs) and allowed to waste for six weeks. Age-matched sham-operated rats are also prepared. (Sham-operated rats are animals that have been exposed to the same surgical procedures as castrated animals except their testes are not removed.) Animals are housed in a temperature-controlled room (24° C.) with a reversed 12 hour light/dark cycle (dark 10:00/22:00) and water and food are available ad libitum.

In order to demonstrate in vivo efficacy, compounds of the present invention are administered daily by transdermal application to the castrated 14 week old rats (body weight about 400-450 g). Animals are randomized based on body weight prior to ascribing a test slot, such that the starting body weights of all treatment groups are within 5% of each other. Test compounds are administered to the animals using conventional vehicles. For example, for transdermal formulation, 81.6% ethanol, 7.6% isopropyl myristate, 9.6% water, 0.4% Carbopol®, 0.826% edetol (ethylenediamine-N,N,N',N'-tetra-2-propanol) is used. Sham operated rats receiving no treatment are used as treatment positive controls whereas castrated rats treated only with vehicle are used as treatment negative controls.

Test animals are dosed transdermally over a two week timeframe with, for example, 0.3, 1, or 5 mg/kg/day of a compound of the present invention. After the two-week treatment, as an indicator of activity, the wet weight of the LA muscle and the BC muscle in the test group is determined and compared to the wet weight of the LA and the BC from the castrated, vehicle-only control group. The wet weights of the muscle obtained in both the test group and the vehicle-only group are normalized relative to total body weight. As an indicator of tissue selective activity, the wet weight of the prostate (P) from test animals is similarly compared to the wet weight of the prostates from the sham control group. Again, the wet weights of the prostates obtained from both the test group and the sham control group are normalized relative to total body weight.

Percent Efficacy (% Eff.) values may be determined as follows: % Eff.=((Wet weight of LA or BC or P in test animal/test animal total body weight)/(Wet weight of LA or BC or P in control animal/control animal total body weight))×100.

Following procedures essentially as described above, the compound of Example 1 displays the following activity in the afore-mentioned rat in vivo model of efficacy and selectivity as shown in Table 11 below:

TABLE 11

| Dose (mg/kg/d), route | LA weight % Efficacy versus control (GDX) (Dunnett's T-test, $p < 0.05$) | BC weight % Efficacy verses control (GDX) (Dunnett's T-test, $p < 0.05$) | P weight % Efficacy versus control (SHAM) (Dunnett's T-test, $p < 0.05$) |
|---|---|---|---|
| 0.03, TD | 114.6 | 106.2 | 3.9 |
| 0.3, TD | 212.5 | 204.4 | 7.3 |
| 1, TD | 237.2 | 272.6 | 11.8 |
| 5, TD | 233.8 | 295.1 | 12.1 |

TD = transdermal route of administration; LA = levator ani muscle; BC = bulbo cavernosus muscle; P = prostate; GDX = gonadectomized Similarly, the compound of Example 2 displays the following activity in the afore-mentioned rat in vivo model of efficacy and selectivity as shown in Table 12 below:

TABLE 12

| Dose (mg/kg/d), route | LA weight % Efficacy versus control (GDX) (Dunnett's T-test, $p < 0.05$) | BC weight % Efficacy verses control (GDX) (Dunnett's T-test, $p < 0.05$) | P weight % Efficacy versus control (SHAM) (Dunnett's T-test, $p < 0.05$) |
|---|---|---|---|
| 0.01, TD | 130.6 | 100.0 | 3.8 |
| 0.1, TD | 230.7 | 199.1 | 7.2 |
| 1, TD | 328.7 | 353.0 | 24.7 |
| 5, TD | 340.6 | 386.5 | 29.0 |

TD = transdermal route of administration; LA = levator ani muscle; BC = bulbo cavernosus muscle; P = prostate; GDX = gonadectomized Collectively, these results demonstrate that Example 1 and Example 2 are Selective Androgen Receptor Modulators (SARMs) that show a dose-dependent increase in the highly responsive striated muscles LA and BC after 2 weeks of treatment, with minimal accrual of androgenic risk (increase in prostate wet weights) in the same animals using a delayed rat gonadectomy model.

In Vivo Model of HDL Cholesterol Lowering Induced by AR Modulators

Cynomolgus monkeys are used for this study, which is conducted to evaluate the effects of androgen receptor modulators on HDL (high-density lipoprotein) cholesterol. This animal model has been shown to respond to androgens by lowering of HDL cholesterol, and is considered predictive of the same response in humans (Nantermet P., et al, *Endocrinol* 149(4):1551-1561).

Young adult female monkeys, approximately 5-8 kg in weight, are individually housed in a climate-controlled room (temperature 72±8° F. and relative humidity 30%-70%) with a 12 hour light/dark cycle and water and food available ad libitum. Compounds of the present invention are administered daily by topical application to 6 monkeys/compound for 2 weeks. If more than one compound is tested in a given study, monkeys are assigned to groups such that each group has similar body weights. Two application sites on the back of the neck are shaved, and compound is applied by spreading over a shaved area using a 1 mL syringe with a 16-gauge needle. Daily application is alternated between the two sites to minimize the potential for skin irritation. Test compounds are administered to the animals using vehicles appropriate for topical application such as a combination of 81.6% ethanol, 7.6% IPM, 9.6% water, 0.4% Carbopol®, and 0.826% edetol (ethylenediamine-N,N,N',N'-tetra-2-propanol). The standard dose volume is 0.15 mL/kg.

Prior to initiation of dosing, blood is drawn from the monkeys on at least 2 days, following an overnight fast, for the purpose of establishing a baseline for clinical pathology parameters (defined as a Chem18+HDL panel, which includes hematology and serum clinical chemistry parameters). The first day of dosing is defined as Day 1. Blood is also drawn three times during the course of the 14-day study (for example, on Days 3, 7 and 13) for evaluation of the Chem18+HDL panel using the Roche Systems Analyzer. Animals are fasted overnight prior to this procedure. Monkeys are observed daily for abnormalities (including skin irritation) and signs of pain or distress. Body weights are collected prior to dosing and near study termination. Blood is also collected for evaluation of pharmacokinetic endpoints, to confirm exposure on Days 1 and 14. Additional parameters are assessed to evaluate the health of the animals.

Following procedures essentially as described above, the compound of Example 1 displays the following activity in the afore-mentioned monkey in vivo model of HDL lowering after 3, 7, and 14 doses as shown in Table 13 below. HDL cholesterol data are expressed as percent decrease relative to the arithmetic mean of two baseline determinations prior to dosing.

TABLE 13

| Dose (mg/kg/day) | After 3 Doses (%) | After 7 Doses (%) | After 14 Doses (%) |
|---|---|---|---|
| 0.035 | 13 | 7.1 | 10 |
| 0.18 | 16 | 29 | 33 |

These data demonstrate that transdermal delivery of the compound of Example 1 has a minimal effect on HDL in monkeys.

We claim:
1. A compound of formula:

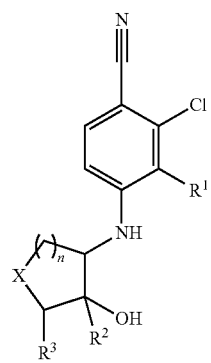

wherein
n is 1 or 2;
X is —CH$_2$— or —O—;
R$^1$ is —CH$_3$ or —CH$_2$CH$_3$;
R$^2$ is —H or —CH$_3$;
R$^3$ is —H or —OH;
wherein R$^3$ is —H when X is —O—;
or a pharmaceutically acceptable salt thereof.
2. A compound of claim 1 of the formula:

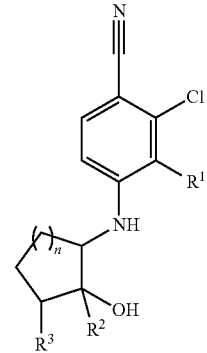

wherein
n is 1 or 2;
R$^1$ is —CH$_3$ or —CH$_2$CH$_3$;
R$^2$ is —H or —CH$_3$;
R$^3$ is —H or —OH;
or a pharmaceutically acceptable salt thereof.
3. A compound of claim 1 of the formula:

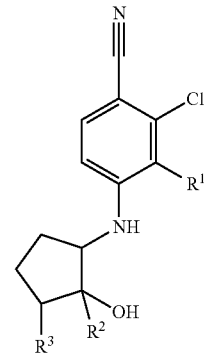

wherein
R¹ is —CH₃ or —CH₂CH₃;
R² is —H or —CH₃;
R³ is —H or —OH;
or a pharmaceutically acceptable salt thereof.

4. A compound of claim 1 of the formula:

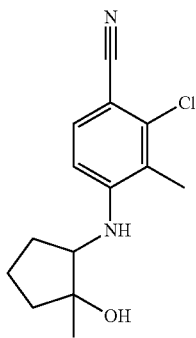 [SMILES: Cc1c(NC2CCCC2(C)O)ccc(C#N)c1Cl]

or a pharmaceutically acceptable salt thereof.

5. A compound of claim 4 having the formula

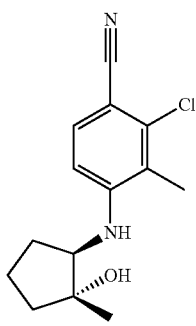 [SMILES: Cc1c(N[C@@H]2CCC[C@@]2(C)O)ccc(C#N)c1Cl]

or a pharmaceutically acceptable salt thereof.

6. A compound of claim 5 that is 2-chloro-4-[[(1R,2R)-2-hydroxy-2-methyl-cyclopentyl]amino]-3-methyl-benzonitrile.

7. A compound of claim 4 having the formula

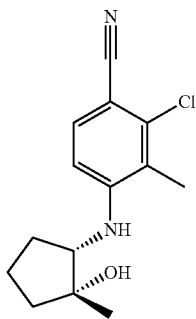 [SMILES: Cc1c(N[C@H]2CCC[C@@]2(C)O)ccc(C#N)c1Cl]

or a pharmaceutically acceptable salt thereof.

8. A compound of claim 7 that is 2-Chloro-4-[[(1S,2R)-2-hydroxy-2-methyl-cyclopentyl]amino]-3-methyl-benzonitrile.

9. A pharmaceutical composition comprising a compound of claim 1, or a pharmaceutically acceptable salt thereof, and one or more pharmaceutically acceptable carriers, diluents, or excipients.

10. A pharmaceutical composition comprising a compound of claim 5, or a pharmaceutically acceptable salt thereof, and one or more pharmaceutically acceptable carriers, diluents, or excipients.

11. A pharmaceutical composition comprising a compound of claim 7, or a pharmaceutically acceptable salt thereof, and one or more pharmaceutically acceptable carriers, diluents, or excipients.

12. A pharmaceutical composition according to claim 9 which is formulated as a patch.

13. A pharmaceutical composition according to claim 9 which is formulated as a topical gel.

14. A pharmaceutical composition according to claim 9 which is formulated as a topical cream.

15. A pharmaceutical composition according to claim 9 which is formulated as a topical spray.

16. A pharmaceutical composition according to claim 9 comprising a solvate.

17. A pharmaceutical composition according to claim 16 comprising 2-chloro-4-[[(1R,2R)-2-hydroxy-2-methyl-cyclopentyl]amino]-3-methyl-benzonitrile•ethanol solvate in crystalline form characterized by an X-ray powder diffraction pattern obtained from a CuKα source which comprises peaks at:

a) 7.00, 17.26, 12.30, and 23.34+/−0.2 in 2θ; or
b) 7.00, 8.59, 12.30, 16.76, 17.26, and 23.34+/−0.2 in 2θ; or
c) 7.00, 8.59, 10.13, 11.89, 12.30, 12.91, 13.95, 16.76, 17.26, 23.34+/−0.2 in 2θ.

18. A method for the treatment of muscle atrophy in a patient comprising administering to a patient in need of such treatment an effective amount of a compound of claim 1, or a pharmaceutically acceptable salt thereof.

19. A method for the treatment of muscle atrophy in a patient comprising administering to a patient in need of such treatment an effective amount of a compound of claim 5, or a pharmaceutically acceptable salt thereof.

20. A method for the treatment of muscle atrophy in a patient comprising administering to a patient in need of such treatment an effective amount of a compound of claim 7, or a pharmaceutically acceptable salt thereof.

21. A method according to claim 18 for the treatment of muscle atrophy associated with hip or knee replacement or hip fracture.

22. A method according to claim 19 for the treatment of muscle atrophy associated with hip or knee replacement or hip fracture.

23. A method according to claim 20 for the treatment of muscle atrophy associated with hip or knee replacement or hip fracture.

* * * * *